United States Patent
Deleyrolle et al.

(10) Patent No.: US 11,020,372 B2
(45) Date of Patent: Jun. 1, 2021

(54) DIETARY AND NATURAL PRODUCT MANAGEMENT OF NEGATIVE SIDE EFFECTS OF CANCER TREATMENT

(71) Applicant: UNIVERSITY OF FLORIDA RESEARCH FOUNDATION, INC., Gainesville, FL (US)

(72) Inventors: Loic Pierre Deleyrolle, Gainesville, FL (US); Brent Allan Reynolds, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 0 days.

(21) Appl. No.: 15/078,590

(22) Filed: Mar. 23, 2016

(65) Prior Publication Data

US 2016/0279094 A1 Sep. 29, 2016

Related U.S. Application Data

(60) Provisional application No. 62/137,535, filed on Mar. 24, 2015.

(51) Int. Cl.
| | |
|---|---|
| *A61K 31/353* | (2006.01) |
| *A61K 31/12* | (2006.01) |
| *A61K 31/26* | (2006.01) |
| *A23L 33/105* | (2016.01) |
| *A23L 33/10* | (2016.01) |
| *A61K 31/23* | (2006.01) |
| *A23L 33/115* | (2016.01) |

(52) U.S. Cl.
CPC ............ *A61K 31/353* (2013.01); *A23L 33/10* (2016.08); *A23L 33/105* (2016.08); *A23L 33/115* (2016.08); *A61K 31/12* (2013.01); *A61K 31/23* (2013.01); *A61K 31/26* (2013.01); *A23V 2002/00* (2013.01)

(58) Field of Classification Search
CPC ...... A61K 31/456; A61K 31/12; A61K 31/26; A61K 31/353
USPC ........................................................ 514/456
See application file for complete search history.

(56) References Cited

U.S. PATENT DOCUMENTS

| | | | |
|---|---|---|---|
| 7,303,770 | B2 | 12/2007 | Fahey et al. |
| 7,968,115 | B2 | 6/2011 | Kurzrock |
| 8,252,831 | B2 | 8/2012 | Kuklish et al. |
| 2009/0143433 | A1 | 6/2009 | Hendrix |
| 2009/0252796 | A1 | 10/2009 | Mazed et al. |
| 2011/0014137 | A1 | 1/2011 | Talalay et al. |
| 2013/0280357 | A1 | 10/2013 | Coy |
| 2013/0287871 | A1 | 10/2013 | Coy |
| 2013/0310457 | A1 | 11/2013 | Ramesh |
| 2014/0193480 | A1 | 7/2014 | McWherter et al. |
| 2014/0275235 | A1 | 9/2014 | Deleyrolle et al. |
| 2014/0350105 | A1 | 11/2014 | D'Agostino et al. |
| 2015/0118306 | A1 | 4/2015 | Cornblatt et al. |
| 2016/0038456 | A1 | 2/2016 | Reynolds et al. |
| 2016/0279094 | A1 | 9/2016 | Deleyrolle et al. |
| 2018/0133194 | A1 | 5/2018 | Deleyrolle et al. |

FOREIGN PATENT DOCUMENTS

| | | |
|---|---|---|
| JP | H1149793 | 2/1999 |
| JP | 2007-153834 | 6/2007 |
| WO | WO 2012/092916 | 7/2012 |
| WO | WO 2012/092917 | 7/2012 |
| WO | WO 2012/113572 | 8/2012 |
| WO | WO 2012/122295 | 9/2012 |
| WO | WO 2012/142511 | 10/2012 |
| WO | WO 2013/186570 | 12/2013 |

(Continued)

OTHER PUBLICATIONS

Du et al., Nutrients (2012), vol. 4(11), pp. 1679-1691.*
Lao et al., BMC Complementary and Alternative Med. (2006), pp. 1-4.*
Shapiro et al., Cancer Epidem., Biomarkers and Prevention (2001), vol. 10, pp. 501-508.*
Nebeling et al., J. Am. Dietetic Assoc. (1995), vol. 95(6), pp. 693-697 (pagination error, p. 694 was missed by the publisher).*
Agerbirk et al. Phytochemistry, 2012, vol. 77, pp. 16-45 (Year: 2012).*

(Continued)

*Primary Examiner* — James D. Anderson
(74) *Attorney, Agent, or Firm* — Saliwanchik, Lloyd & Eisenschenk

(57) ABSTRACT

The invention relates to novel methods and compositions for safely reducing negative side effects of cancer treatments. These methods and compositions comprise administering to a patient a composition comprising one or more of the following: curcumin (derived from turmeric), epigallocatechin-3-gallate (EGCG, enriched in green tea), glucosinolates (enriched in cruciferous vegetables) and/or derivatives thereof, such as sulforaphane (SFN), alone or combined with a ketogenic diet or a modified ketogenic diet. Also the current invention relates to a composition comprising medium chain triglycerides (MCT), Epigallocatechin-3-gallate, curcumin, compositions comprising glucosinolates and/or derivatives thereof, such as sulforaphane (SFN). The invention provides that administering a composition comprising curcumin, EGCG, sulforaphane, alone or combined with a ketogenic diet or a modified ketogenic diet (low carbohydrate diet) alone or supplemented with MCT improves resistance of normal cells to cytotoxicity of cancer treatments, in turn, reducing their negative side effects. Increasing normal cells, tissues or organs' resistance to chemotherapeutic agents, the invention improves patients' tolerance to anti-cancer treatments' toxicity, which, in turn, contributes to enhance their efficacy, leading to increased survival of the subject treated with the current invention.

20 Claims, 14 Drawing Sheets

(56) References Cited

FOREIGN PATENT DOCUMENTS

| WO | WO 2014/008366 | 1/2014 |
|---|---|---|
| WO | WO 2014/159500 | 10/2014 |
| WO | WO 2014/168736 | 10/2014 |
| WO | WO 2015/034812 | 3/2015 |
| WO | WO 2016/210405 | 12/2016 |

OTHER PUBLICATIONS

Farooqi, A. et al., "Shattering the underpinnings of neoplastic architecture in LNCaP: synergistic potential of nutraceuticals in dampening PDGFR/EGFR signaling and cellular proliferation" *Journal of Experimental Therapeutics and Oncology*, 2011, pp. 201-206, vol. 9.

Jeong, W. et al., "Modulation of AP-1 by Natural Chemopreventive Compounds in Human Colon HT-29 Cancer Cell Line" *Pharmaceutical Research*, Apr. 2004, pp. 649-660, vol. 21, No. 4.

Boado, R.J., et al., "Gene expression of GLUT3 and GLUT1 glucose transporters in human brain tumors," *Molecular Brain Research*, 1994, vol. 27, pp. 51-57.

Deleyrolle, L.P., et al., "Evidence for label-retaining tumour-initiating cells in human glioblastoma," *Brain*, 2011, vol. 134, pp. 1331-1343.

Fotovati, A., et al., "YB-1 Bridges Neural Stem Cells and Brain Tumor-Initiating Cells via Its Roles in Differentiation and Cell Growth," *Cancer Research*, 2011, vol. 71, No. 16, pp. 5569-5578.

Gao, Y., et al., "Inhibition of Y-box binding protein-1 slows the growth of glioblastoma multiforme and sensitizes to temozolomide independent $O^6$-methylguanine-DNA methyltransferase," *Molecular Cancer Therapeutics*, Dec. 2009, vol. 8, No. 12, pp. 3276-3284.

Kohsaka, S., et al., "STAT3 Inhibition Overcomes Temozolomide Resistance in Glioblastoma by Downregulating MGMT Expression," *Molecular Cancer Therapeutics*, 2012, vol. 11, No. 6, pp. 1289-1299.

Le Calvé, B., et al., "Long-term In Vitro Treatment of Human Glioblastoma Cells with Temozolomide Increases Resistance In Vivo through Up-regulation of GLUT Transporter and Aldo-Keto Reductase Enzyme AKR1C Expression," *Neoplasia*, 2010, vol. 12, No. 9, pp. 727-739.

Redon, C.E., et al., "Tumors induce complex DNA damage in distant proliferative tissues in vivo," *PNAS*, Oct. 19, 2010, vol. 107, No. 42, pp. 17992-17997.

Sherry, M.M., et al., "STAT3 Is Required for Proliferation and Maintenance of Multipotency in Glioblastoma Stem Cells," *Stem Cells*, 2009, vol. 27, pp. 2383-2392.

Siebzehnrubl, F.A., et al., "The ZEB1 pathway links glioblastoma initiation, invasion and chemoresistance," *EMBO Molecular Medicine*, 2013, vol. 5, pp. 1196-1212.

Written Opinion in International Application No. PCT/US2014/023934, dated Aug. 26, 2014, pp. 1-9.

Otto, C. et al. "Growth of human gastric cancer cells in nude mice is delayed by a ketogenic diet supplemented with omega-3 fatty acids and medium-chain triglycerides" *BMC Cancer*, Apr. 30, 2008, pp. 1-12, vol. 8, No. 122.

Baranano, K. W. et al. "The Ketogenic Diet: Uses in Epilepsy and Other Neurologic Illnesses" *Current Treatment Options in Neurology*, Nov. 2008, pp. 410-419, vol. 10, No. 6.

Papi, A. et al. "Cytotoxic and Antioxidant Activity of 4-Methylthio-3-butenyl Isothiocyanate from *Raphanus sativus* L (Kaiware Dalkon) Sprouts" *Journal of Agricultural and Food Chemistry*, 2008, pp. 875-883, vol. 56, No. 3.

Li, Y. et al. "Implications of cancer stem cell theory for cancer chemoprevention by natural dietary compounds" *Journal of Nutritional Biochemistry*, 2011, pp. 799-806, vol. 22.

Office Action for U.S. Appl. No. 14/197,897, dated Oct. 20, 2016, pp. 1-16.

Basnet, P. et al. "Curcumin: An Anti-Inflammatory Molecule from a Curry Spice on the Path to Cancer Treatment" *Molecules*, 2011, pp. 4567-4598, vol. 16.

Navarro-Peran, E. et al. "The anti-inflammatory and anti-cancer properties of epigallocatechin-3-gallate are mediated by folate cycle disruption, adenosine release and NF-κB suppression" *Inflammation Research*, 2008, pp. 472-478, vol. 57.

Cheung, K. L. et al. "Synergistic Effect of Combination of Phenethyl Isothiocyanate and Sulforaphane or Curcumin and Sulforaphane in the Inhibition of Inflammation" *Pharmaceutical Research*, Jan. 2009, pp. 224-231, vol. 26, No. 1.

"Low-Carbohydrate, High-Protein Diets May Reduce Both Tumor Growth Rates and Cancer Risk" *Science Daily*, Jun. 14, 2011, pp. 1-3, obtained from internet on Apr. 20, 2012: http://www.sciencedaily.com/releases/2011/06/110614115037.htm.

Chan, A. "Low-Carb, High-Protein Diet Slows Cancer Growth in Mice, Study Finds" Huffington Post, Jun. 14, 2011, pp. 1-2, obtained from internet on Apr. 20, 2012: http://www.huffingtonpost.com/2011/06/14/low-carb-high-protein-die_n_876645.html.

Dowling, R. J. et al. "Understanding the benefit of metformin use in cancer treatment" *BMC Medicine*, 2011, pp. 1-6, vol. 9, No. 33.

Zhou, W. et al. "The calorically restricted ketogenic diet, an effective alternative therapy for malignant brain cancer" *Nutrition & Metabolism*, 2007, pp. 1-15, vol. 4, No. 5.

Klement, R. J. et al. "Is there a role for carbohydrate restriction in the treatment and prevention of cancer?" *Nutrition & Metabolism*, 2011, pp. 1-16, vol. 8, No. 75.

Ho, V. W. et al. "A Low Carbohydrate, High Protein Diet Slows Tumor Growth and Prevents Cancer Initiation" *Cancer Research*, Jul. 1, 2011, pp. 4484-4493, vol. 71.

Universitatsklinikum Wurzburg, "Information on a ketogenic (low carbohydrate / high fat + protein) diet for cancer patients", 2009, pp. 1-31, obtained from http://www.frauenklinik.uni-wuerzburg.de/forschung/ketogenic english.htm.

Tisdale, M. J. et al. "Reduction of weight loss and tumour size in a cachexia model by a high fat diet" *Br. J. Cancer*, 1987, pp. 39-43, vol. 56.

Stan, S. D. et al. "Bioactive Food Components and Cancer Risk Reduction" *Journal of Cellular Biochemistry*, 2008, pp. 339-356, vol. 104.

Kozluca, O. et al. "Prevention of doxorubicin induced cardiotoxicity by catechin" *Cancer Letters*, 1996, pp. 1-6, vol. 99.

Lee, W.-L. et al. "Phytoagents for Cancer Management: Regulation of Nucleic Acid Oxidation, ROS, and Related Mechanisms" *Oxidative Medicine and Cellular Longevity*, 2013, pp. 1-22, vol. 2013, Article ID 925804.

Gaona-Gaona, L. et al. "Protective effect of sulforaphane pretreatment against cisplatin-induced liver and mitochondrial oxidant damage in rats" *Toxicology*, 2011, pp. 20-27, vol. 286.

Seyfried, T. N. et al. "Targeting energy metabolism in brain cancer: review and hypothesis" *Nutrition & Metabolism*, 2005, pp. 1-9, vol. 2, No. 30.

Waseem, M. et al. "Mitochondrial dysfunction mediated cisplatin induced toxicity: Modulatory role of curcumin" *Food and Chemical Toxicology*, 2013, pp. 334-342, vol. 53.

Nebeling, L. C. et al. "Effects of a ketogenic diet on tumor metabolism and nutritional status in pediatric oncology patients: two case reports" *J. Am Coll Nutr*, Apr. 1995, pp. 202-208, vol. 14, No. 2.

Bachstetter, A. D. et al. "Spirulina Promotes Stem Cell Genesis and Protects against LPS Induced Declines in Neural Stem Cell Proliferation" *PLoS One*, May 2010, pp. 1-11, vol. 5, Issue 5, e10496.

Kelsey, N. A. et al. "Nutraceutical Antioxidants as Novel Neuroprotective Agents" *Molecules*, Nov. 3, 2010, pp. 7792-7814, vol. 15.

Maalouf, M. et al. "The neuroprotective properties of calorie restriction, the ketogenic diet, and ketone bodies" *Brain Research Reviews*, 2009, pp. 293-315, vol. 59.

Martuscello, R. T. et al. "A Supplemental High-Fat Low-Carbohydrate Diet for the Treatment of Glioblastoma" *Clinical Cancer Research*, Dec. 2, 2015, pp. 2482-2495, vol. 22, No. 10.

Seyfried, T. N. et al. "Targeting Energy Metabolism in Brain Cancer with Restricted Diets" *Glioblastoma*, Sep. 18, 2009, pp. 341-363.

Li et al. "Impact on DNA methylation in cancer prevention and therapy by bioactive dietary components" *Curr. Med. Chem.*, 2010, vol. 17(20), pp. 2141-2151.

(56) References Cited

OTHER PUBLICATIONS

Fusimi, K. "Can Simian Virus 40 be the factor of human tumor outbreaks?", *Tiss. Cult. Res. Commun.*, 1997, vol. 16, pp. 181-187, summary.

Chung, M-Y. et al. "Molecular mechanisms of chemopreventive phytochemicals against gastroenterological cancer development" *World J. Gastroenterol.*, 2013, 19(7):984-993.

Schmitz, K. et al. "'Disease modifying nutricals' for multiple sclerosis" *Pharmacology & Therapeutics*, 2015, 148:85-113.

Biao, J. Health Caring with Daikon Radish, Nov. 30, 2010; in Chinese.

Biao, J. Health Caring with Daikon Radish, Nov. 30, 2010; English translation of relevant portion.

Office Action dated Sep. 10, 2018; Chinese Patent Application No. 201480028215.2.

Riken, K. "Discovery of a novel gene allowing brassica vegetables to make cancer-preventing components, -New way to develop health-functional vegetables", Press release graspable in 60 seconds, DNA Research Institute, Apr. 10, 2007; in Japanese.

Riken, K. "Discovery of a novel gene allowing brassica vegetables to make cancer-preventing components, -New way to develop health-functional vegetables", Press release graspable in 60 seconds, DNA Research Institute, Apr. 10, 2007; English translation of relevant portion.

Office Action dated Oct. 23, 2018; Japanese Patent Application No. 2016-501388.

Office Action dated Nov. 23, 2018; U.S. Appl. No. 14/197,897.

Currently pending claims in U.S. Appl. No. 14/197,897.

Currently pending claims in U.S. Appl. No. 15/578,601.

Office Action dated Nov. 2, 2018; U.S. Appl. No. 14/775,751.

Currently pending claims in U.S. Appl. No. 14/775,751.

Khalife, S. et al. "Molecular targets of natural health products in arthritis" *Arthritis Research & Therapy*, 2011, vol. 13, p. 102 (3 pages).

Kong, J-S. et al. "Inhibition of Synovial Hyperplasia, Rheumatoid T Cell Activation, and Experimental Arthritis in Mice by Sulforaphane, a Naturally Occurring Isothiocyanate" *Arthritis & Rheumatism*, 2010, pp. 159-170, vol. 62, No. 1.

Davidson, R. et al. "Sulforaphane Represses Matrix-Degrading Proteases and Protects Cartilage From Destruction in Vitro and in Vivo" *Arthritis & Rheumatism*, 2013, 65(12):3130-3140.

Davidson, R. et al. "Isothiocyanates are detected in human synovial fluid following broccoli consumption and can affect the tissues of the knee joint" *Scientific Reports*, 2017, 7:3398 (10 pages).

Fahey, J. et al. "Broccoli sprouts: An exceptionally rich source of inducers of enzymes that protect against chemical carcinogens" *Proc. Natl. Acad. Sci. USA*, 1997, 94:1036710372.

Thysen, S. et al. "Targets, models and challenges in osteoarthritis research" *Disease Models & Mechanisms*, 2015, 8:17-30.

Sporn, M. and Harris, E. "Proliferative diseases" *Am. J. Med.*, 1981, 70(6):1231-1235, abstract.

Illustration, Well-understandable agriculture technology innovation, Agriculture can be industrialized and adaptable to IT (Information Technology) this far., Oct. 27, 2011, first edition, first printing, pp. 68-69 (additionally cited literature, showing well-known technology).

Office Action dated Dec. 17, 2019; Japanese Patent Application No. 2018-093204, pp. 1-6.

Vyas, D. et al. "Chemotherapy-enhanced inflammation may lead to the failure of therapy and metastasis" *OncoTargets and Therapy*, 2014, 7:1015-1023.

\* cited by examiner

DIETARY AND NATURAL PRODUCT MANAGEMENT OF NEGATIVE SIDE EFFECTS OF CANCER TREATMENT

BACKGROUND OF THE INVENTION

The management of many cancers involves a combination of treatments often employing surgery followed by chemotherapy, both targeted and non-targeted, with or without radiation. Anti-cancer protocols are associated with a number of toxicities and negative effects that can affect non-cancerous cells and/or the normal function of one or more organs or organ systems. These include but not limited to damage to critical organs [liver, kidneys, pancreas, brain, and heart], hematologic toxicity [such as neutropenia, thrombocytopenia, anemia], damage to peripheral nerves [neuropathy], fatigue, and anxiety/distress. Often the negative side effects of these treatments can be dose limiting and/or result in the suspension of treatment, both, which are associated with decreased efficacy of treatment.

We have developed a treatment aimed at attenuating the negative side effects of cancer treatments such as chemotherapy and radiation. The treatment protocol involves a dietary component together with the simultaneous oral consumption of 4 natural products. The nutritional formulation involves altering one's dietary intake of carbohydrates [in the 10 to 20% range] in addition to consuming medium chain triglycerides [MCT], an extract from green tea [EGCG], curcumin and freeze-dried broccoli sprouts. When used together we have found this dietary intervention to be effective at attenuating chemotherapy-induced peripheral neuropathy, neutropenia, anemia, damage to essential organs and to provide a protective function of endogenous stem cell pools.

BRIEF SUMMARY OF THE INVENTION

The disclosed invention relates to methods and formulations to protect patients from toxic and negative side effects related to cancer treatments. More specifically, the invention provides dietary methods and formulations of natural products that are able to protect a patient's normal cells, tissues and organs from the undesirable side effects of cancer treatments without compromising the killing of malignant cells.

There are few to no products available to attenuate the negative side effects of cancer treatments. For example, chemotherapy induced peripheral neuropathy there are no effective treatments. Neutropenia is currently treated with Filgrastim, which stimulates the bone marrow to increase production of neutrophils. Anemia is treated with blood transfusion or Epoetin, however each has its own particular negative side effects. There are no treatments for managing the damage done to essential organs such as the liver, kidneys, pancreas and brain.

Our approach differs from the few treatments that are available for treating these complications related to cancer treatments in that our methods are preventing the damage as opposed to treating the problem or damage once it has already arose.

Our composition involves the use of:

1. Low carbohydrate [LC] diet: the typical North American diet provides approximately 50 to 60% of its caloric intake from carbohydrates. As carbohydrates are the main source of glucose and the primary source of energy for glucose stored tumor cells, reducing carbohydrates through dietary restrictions can assist in lowering glucose levels and hence limiting tumor cell access to this fuel source. A diet composed of 10 to 20% carbohydrates [as opposed to 50-60%] has been shown to reduce glucose levels in humans. Preclinical animal studies have demonstrated that carbohydrate-restricted diets can significantly slow tumor progression and extend life span.

2. Medium chain triglycerides [MCT]: fractionated from coconuts or Palm kernel oils MCTs are used clinically for patients with malabsorption symptoms. Due to their small molecular size MCT are digested rapidly traveling directly to the liver where they are quickly metabolize and elevate ketones levels. Increased ketones and reduced glucose are the primary physiological events that underlie the ketogenic diet [a diet composed of 90% fat and 10% proteins/carbohydrates] and have been demonstrated to reduce tumor cell proliferation, cancer progression and extent life expectancy in preclinical models. There are a number of case reports revealing positive effects of a ketogenic diet in pediatric and adult tumor patients 3. Curcumin: derived from turmeric, curcumin have a demonstrated anti-inflammatory and anti-cancer effect on both the initiation and progression of solid tissue tumors.

4. Epigallocatechin-3-gallate (EGCG): EGCG is most abundant catechin found in green tea. There is a large body of literature administering effectiveness on reducing tumor proliferation, down regulating tumor promoting pathways and safety in humans.

5. Freeze-dried broccoli sprouts (containing glucosinolates and enzymatic degradation products such as isothiocyanates, glucoraphanin, glucoerucin, Indole-3-carbinol [I3C], sulforaphane [SFN] and erucin [ERN]): Each of these are bioactive molecules found in cruciferous vegetables. They are found in highest concentration in broccoli sprouts. There is a growing body of preclinical data supporting efficacy as anticancer agents and several clinical studies have demonstrated their safety. Effective doses of glucosinolates and their enzymatic breakdown products can be delivered by consuming broccoli sprouts or broccoli sprout powder.

Treatments composition is as follow: [1] Control=55% carbohydrates, 30% proteins, 15% fat, [2] MCT/LC/Curcumin/EGCG/SFN=10-20% carbohydrates, 50-60% fat (about half corning from MCT), 30% Proteins+Curcumin [1200 mg/kg of body weight], EGCG [1200 mg/kg of body weight]), SFN [25 mg/kg of body weight].

Figure 2:
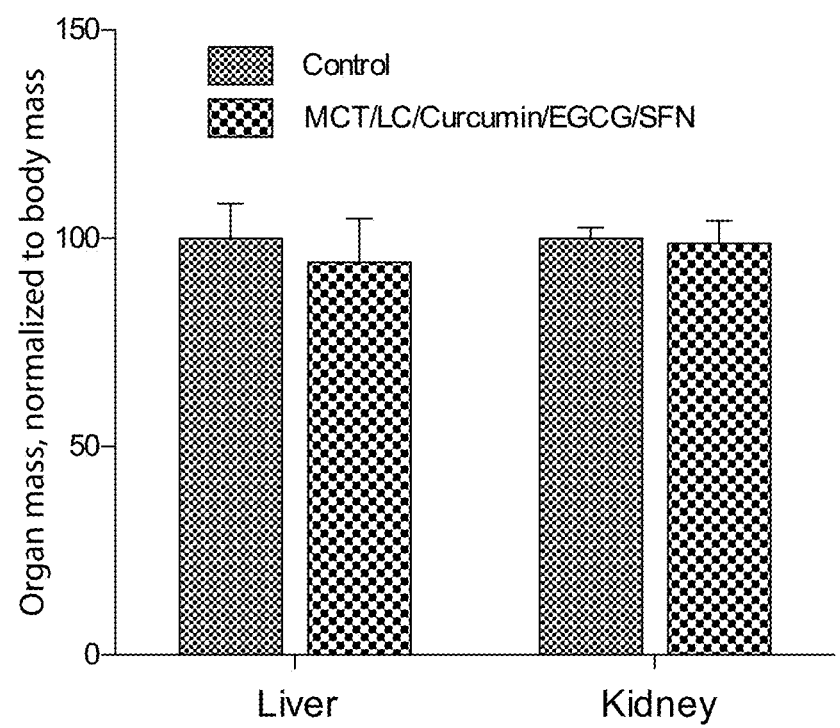

FIG. 2: Organs-targeted toxicity. Toxicity of MCT/LC/Curcumin/EGCG/SFN was further assessed after 4 weeks of treatment via comparing the mass of the organs liver and kidney (normalized to body weight). No difference was observed between the experimental group and controls.

Figure 3:
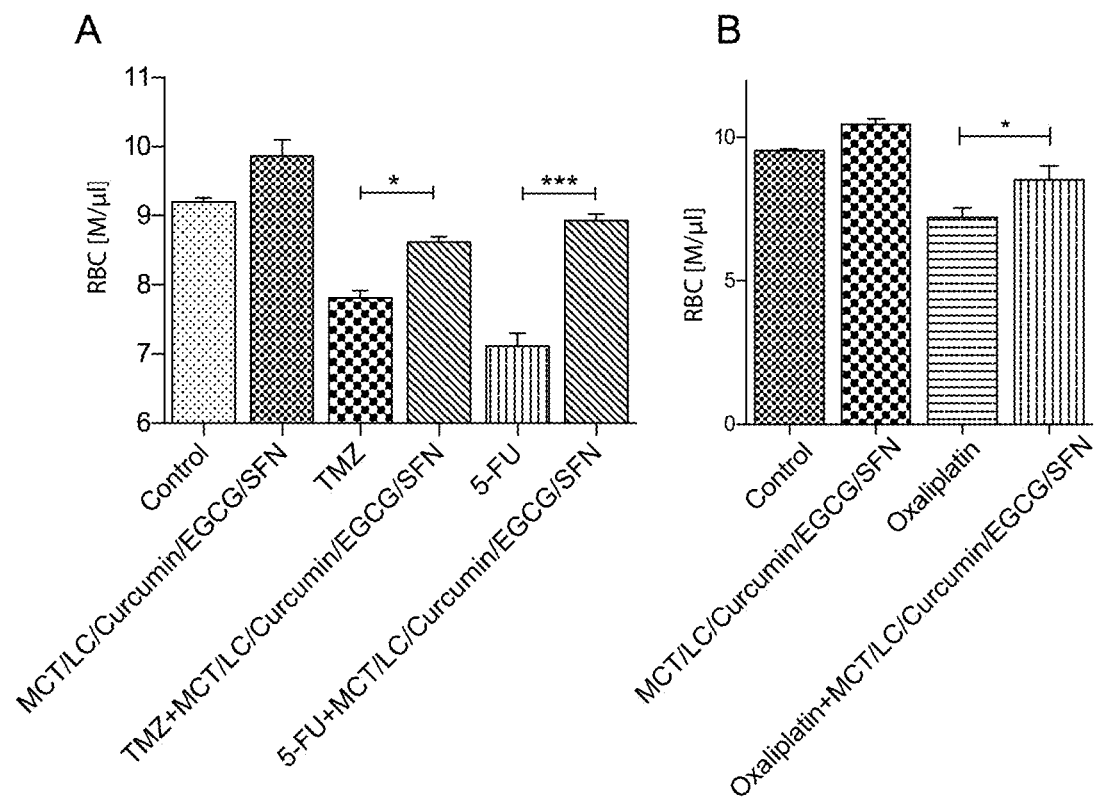

FIG. 3: MCT/LC/Curcumin/EGCG/SFN prevents chemotherapy-induced RBC reduction. Hematology study revealed the ability of our experimental treatment to minimize the decrease of red blood cells associated with chemotherapy ([A]20 mg/kg TMZ, 100 mg/kg 5-FU, [B] 40 mg/kg oxaliplatin). ***, p<0.001, *, p<0.05, one-way ANOVA.

Figure 4:
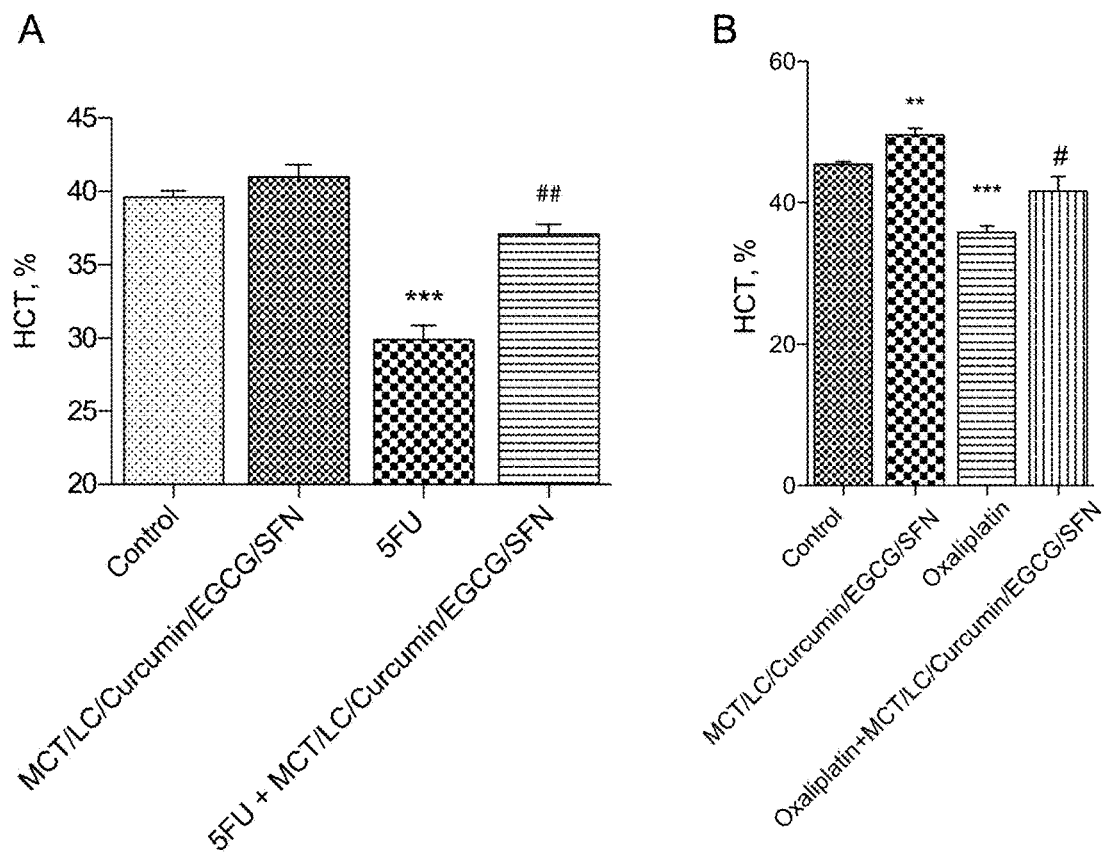

FIG. 4: MCT/LC/Curcumin/EGCG/SFN prevents chemotherapy-induced hematocrit reduction. Hematology study showed the ability of MCT/LC/Curcumin/EGCG/SFN to minimize the decrease of hematocrit associated with chemotherapy ([A] 100 mg/kg 5-FU, [B] 40 mg/kg oxaliplatin). *, p<0.001, , p<0.01, one-way ANOVA, compared to control. ## p<0.01, #, p<0.05, one-way ANOVA, compared to chemotherapeutic agents.

Figure 5:
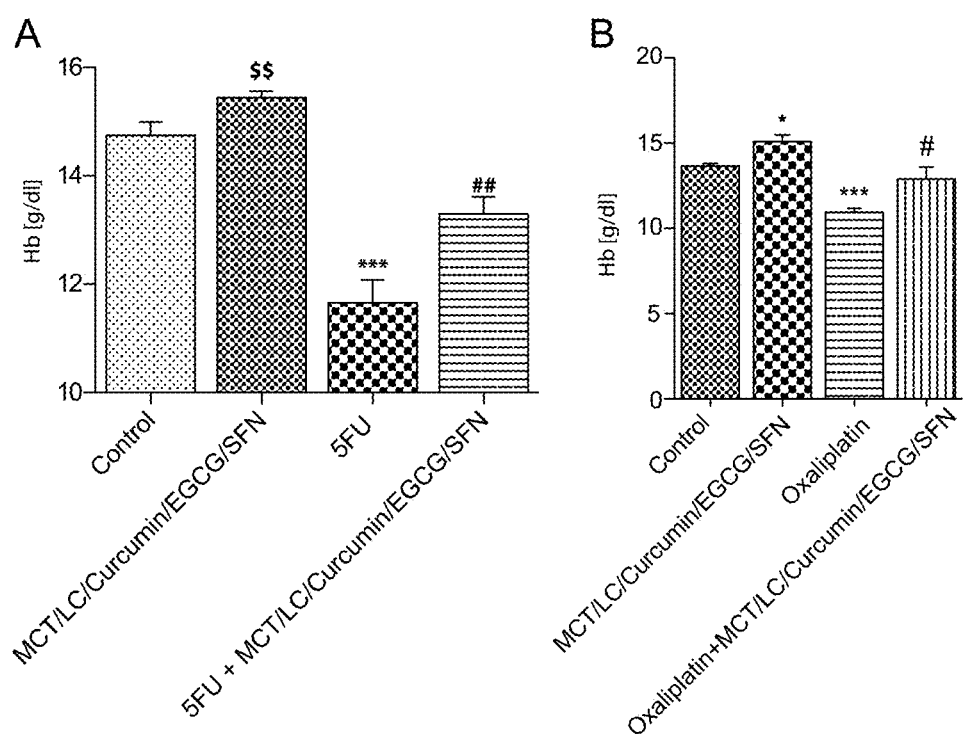

FIG. 5: MCT/LC/Curcumin/EGCG/SFN alleviates chemotherapy-induced hemoglobin reduction. Hemoglobin level was significantly diminished when animals were treated with 100 mg/kg 5-FU or 40 mg/kg oxaliplatin. When combined with MCT/LC/Curcumin/EGCG/SFN, the chemotherapeutic agents were less toxic and the level of hemoglobin was significantly less reduced. Of note, MCT/LC/Curcumin/EGCG/SFN increased hemoglobin level compared to controls. ***, p<0.001, *, p<0.05, one-way ANOVA, compared to control. ##, p<0.01, p<0.05, one-way ANOVA, compared to chemotherapeutic agents. $^{\$\$}$, p<0.01, t-test, compared to control.

Figure 6:
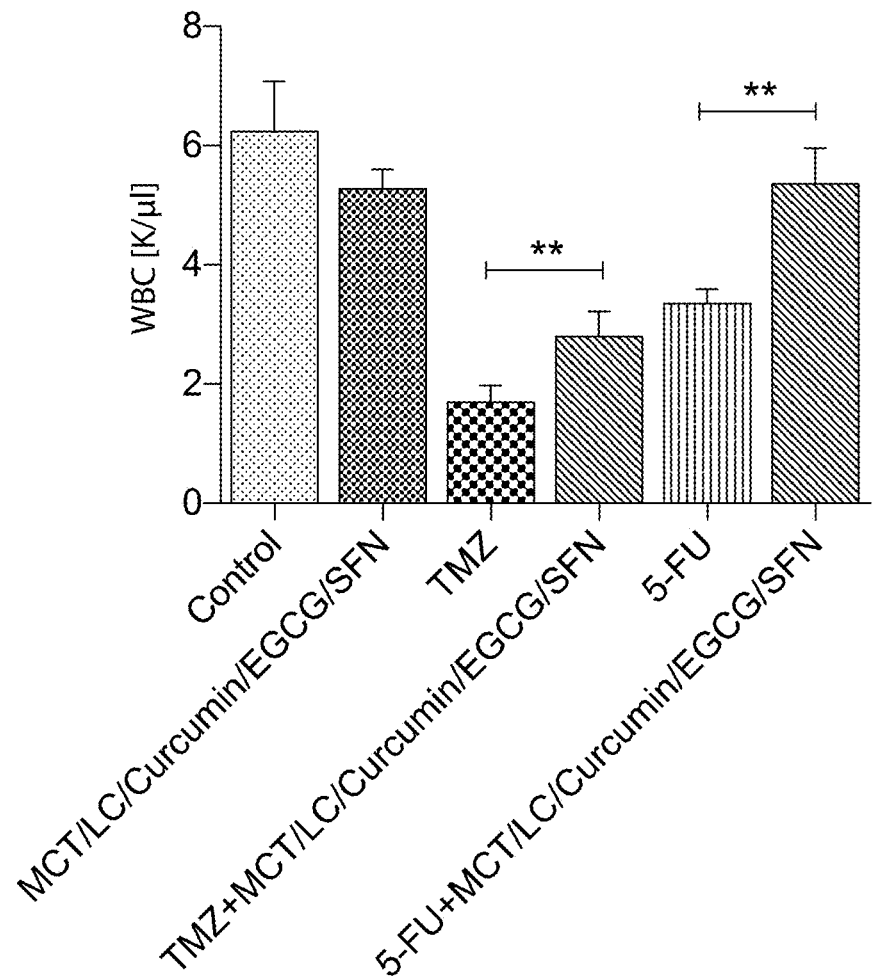

FIG. 6: MCT/LC/Curcumin/EGCG/SFN mitigates chemotherapy-induced WBC reduction. Hematology study also demonstrated the ability of our treatment to limit the decrease of white blood cells related chemotherapy treatment (20 mg/kg TMZ, 100 mg/kg 5-FU). ***, *, p<0.001, p<0.05, one-way ANOVA.

Figure 7:
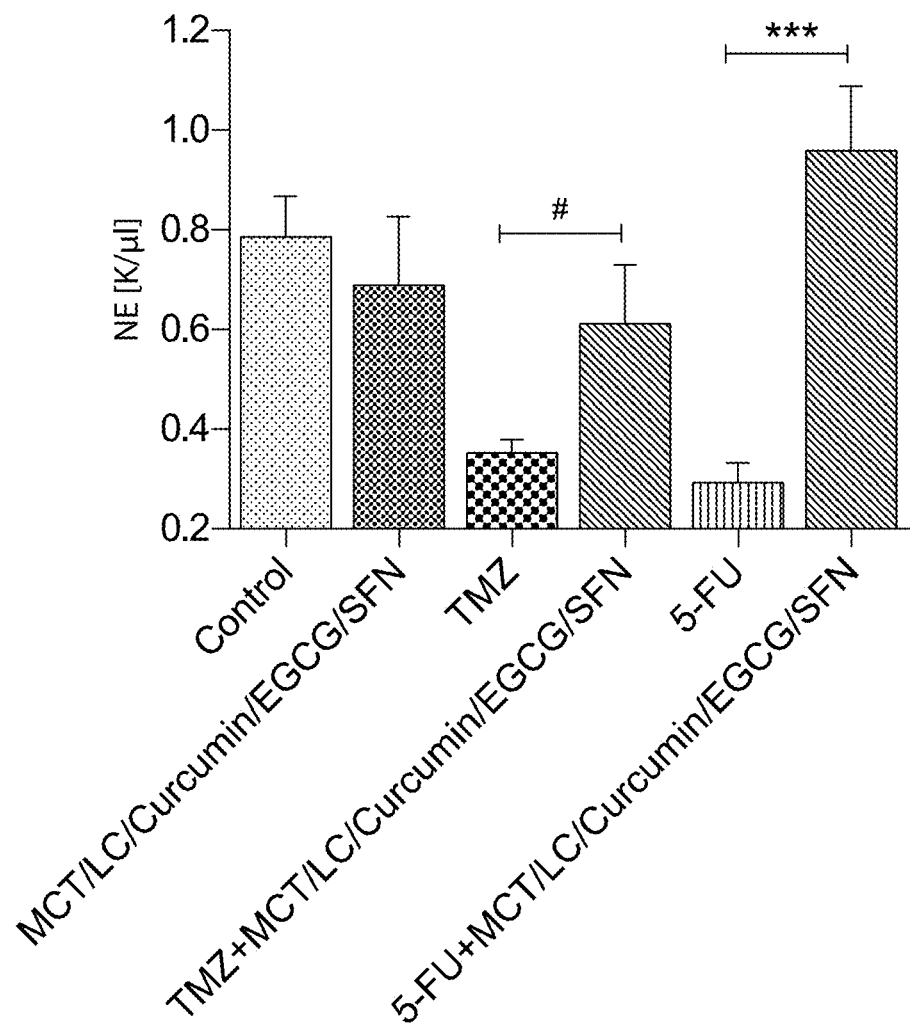

FIG. 7: MCT/LC/Curcumin/EGCG/SFN prevents chemotherapy-induced neutrophils reduction. Our experimental treatment minimizes the decrease of neutrophils associated with chemotherapy (100 mg/kg 5-FU). ***, p<0.001, one-way ANOVA. #, p<0.05, t-test.

Figure 8:
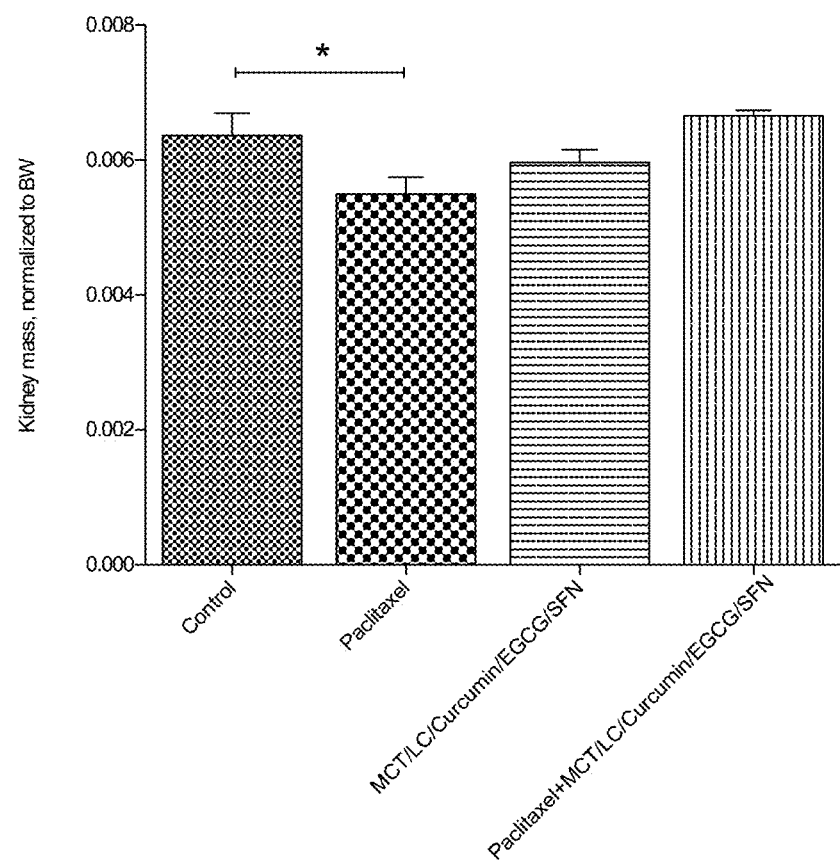

FIG. 8: MCT/LC/Curcumin/EGCG/SFN prevents chemotherapy-induced nephrotoxicity. Targeted toxicity of the chemotherapeutic agent Paclitaxel was assessed after 3-4 weeks of treatment via measuring the mass of the kidneys. The standard chemotherapy drug Paclitaxel [5 mg/kg] induces a significant diminution of the kidney weight that is prevented by combining the drug with our experimental treatment. This data suggests a nephroprotective effect of our treatment in the context of cancer treatment protocol using Paclitaxel. *, p<0.05, t-test.

Figure 9:
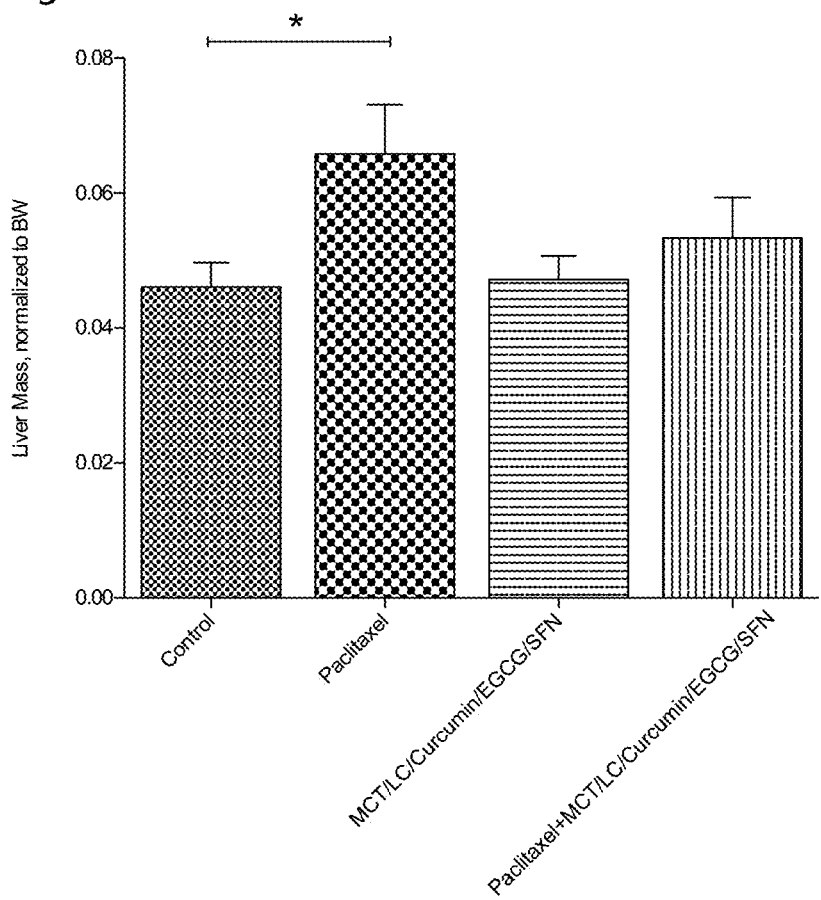

FIG. 9: MCT/LC/Curcumin/EGCG/SFN prevents chemotherapy-induced hepatotoxicity. Toxicity was assessed after 3-4 weeks of treatment via comparing the mass of the liver. The standard chemotherapy drug Paclitaxel [5 mg/kg] induces a significant liver enlargement that is prevented by combining the drug with MCT/LC/Curcumin/EGCG/SFN. This data reveals anti-hepatotoxicity properties of our treatment in cancer treatment protocol using Paclitaxel. *, p<0.05, t-test.

Figure 10:
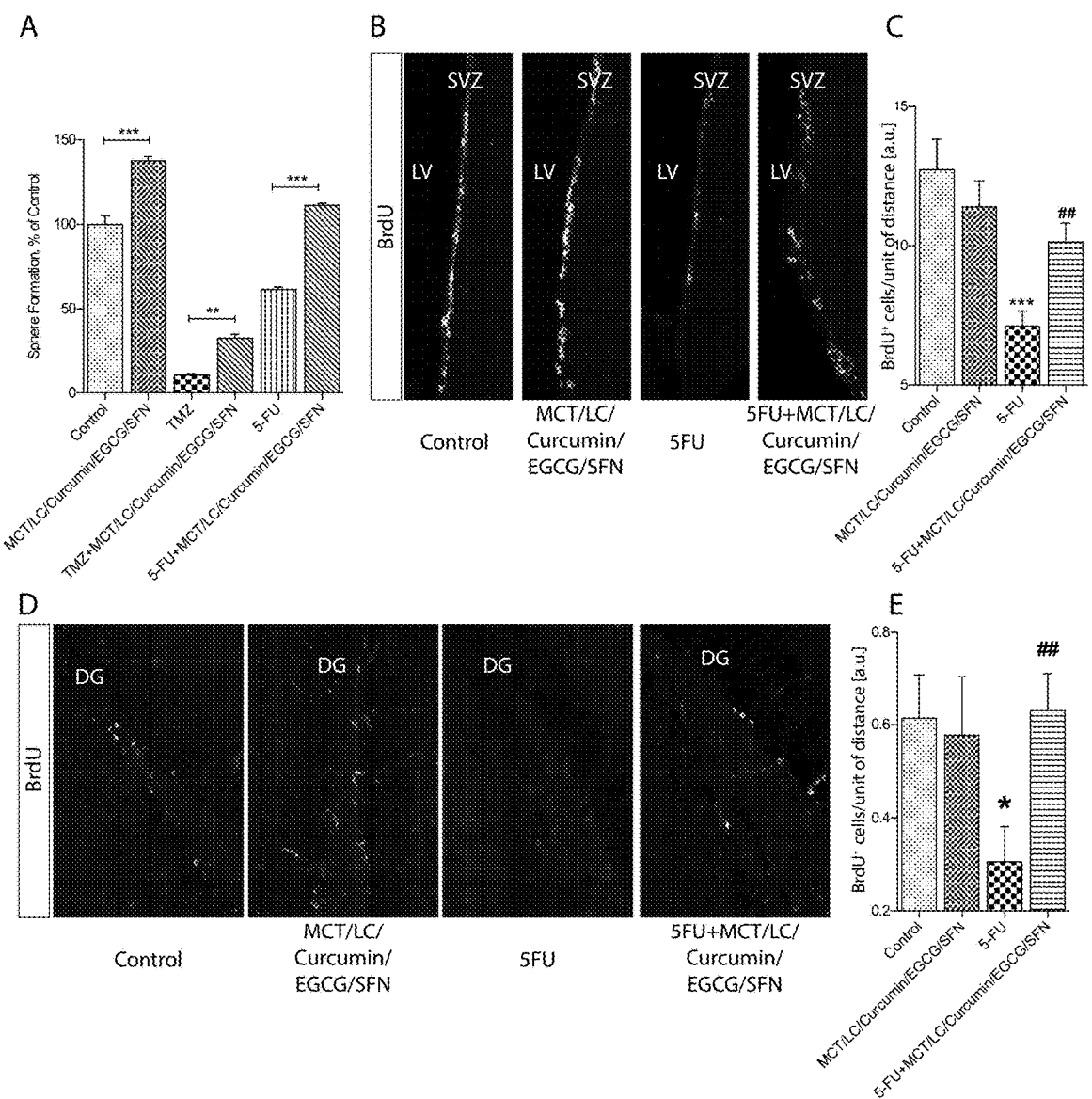

FIG. 10: MCT/LC/Curcumin/EGCG/SFN stimulates neural stem cell activity and prevents chemotherapy to alter neural stem cell proliferation. A] Periventricular cells from the brains of animals treated with the indicated treatments were isolated and cultured in the neurosphere assay at clonal density to quantify clonogenic frequency. Our experimental treatment induced a significant increase in neurosphere formation compared to controls. Chemotherapies induced a decline of neural stem cell activity seen by decreased neurosphere formation, which can be improved when combined with our treatment, , *, p<0.01, p<0.001, one-way ANOVA. B-C] Animals treated with MCT/LC/Curcumin/EGCG/SFN did not demonstrate any decrease in neural stem cell (NSC) activity (BrdU immunoreactivity) in the sub-ventricular area (SVZ) compared to the control group. The results also show the targeting of NSCs by 5-FU as demonstrated by the reduced level of BrdU+ve cells in the periventricular area of the brain of animal treated with the chemo agent. However, we observed a protective effect of MCT/LC/Curcumin/EGCG/SFN on NSC activity when combined with 5-FU. The combination treatment increased NSC activity to a level similar to controls. ***, p<0.001, one-way ANOVA, compared to control, ##, p<0.01, t-test, compared to 5-FU. D-E] NSC activity was also measured in the hippocampus, region of the brain involved in cognition. Similarly, MCT/LC/Curcumin/EGCG/SFN showed a protective effect when combined with 5-FU. *, p<0.05, one-way ANOVA, compared to control. ##, p<0.01, t-test, compared to 5-FU.

Figure 11:
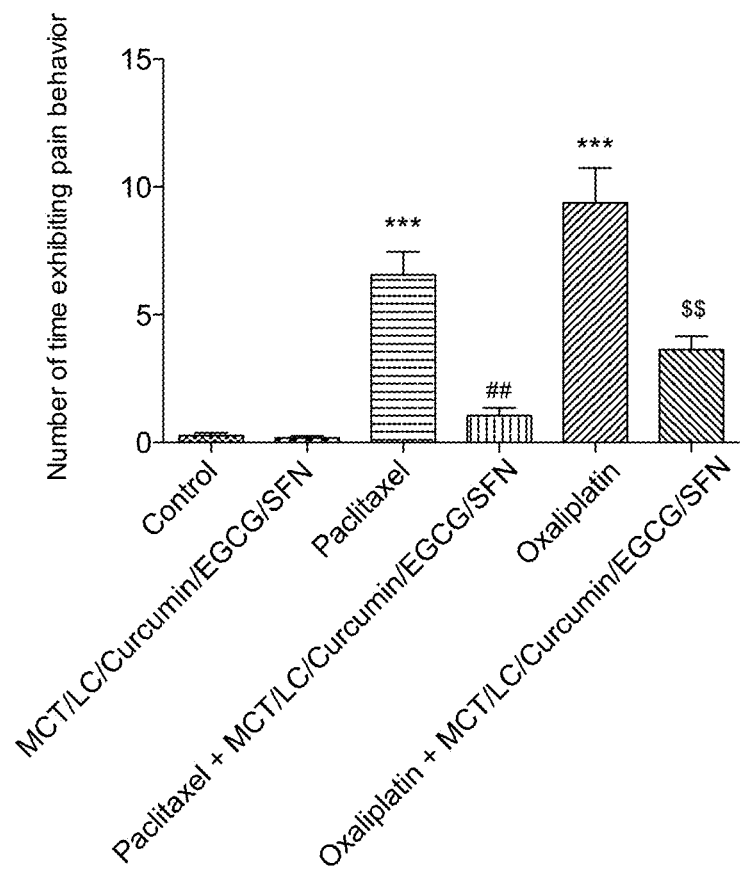

FIG. 11: MCT/LC/Curcumin/EGCG/SFN inhibits chemotherapy-induced peripheral neuropathy (CIPN).

Cold allodynia assay was performed, where one drop of acetone was applied to the plantar surface of the hindpaw using a 1 ml syringe. Mice were observed for 2.5 min after each acetone application. Spontaneous pain behavior (defined as shaking, flinching, or licking of the paw as well as holding the paw in an elevated position) that occurred within 2.5 min after acetone application was counted as a positive response. Spontaneous pain behavior that occurred within the first 15 s after acetone application was not counted, since most mice had some reaction to the initial application. The number of time animals were exhibiting pain behavior (including licking, limping and shaking) was recorded and compared between Control, Paclitaxel, Oxaliplatin, Paclitaxel+MCT/LC/Curcumin/EGCG/SFN, and Oxaliplatin+MCT/LC/Curcumin/EGCG/SFN treated mice. These results show the ability of our treatment to limit the level of CIPN. ***, p<0.001, one-way ANOVA, compared to controls. ##, p<0.01, one-way ANOVA, compared to paclitaxel. $^{\$\$}$, p<0.01, one-way ANOVA, compared to oxaliplatin.

Figure 12:
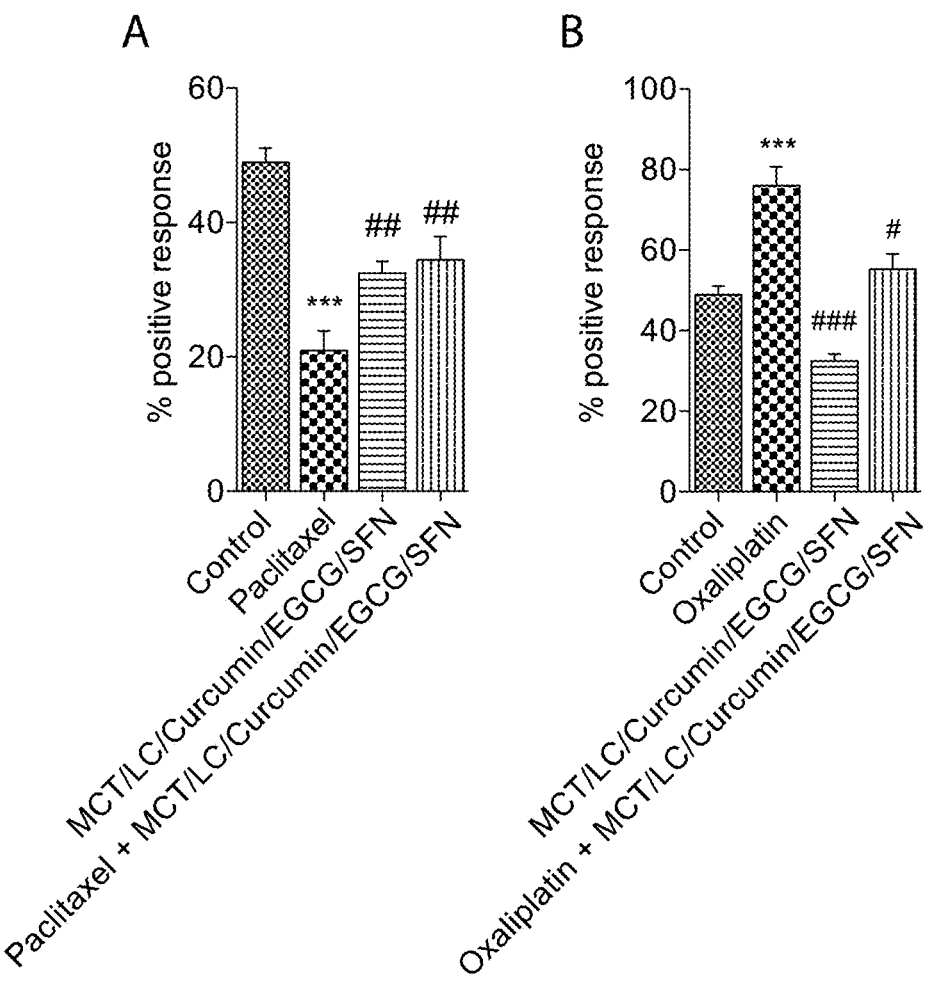

FIG. 12: MCT/LC/Curcumin/EGCG/SFN inhibits chemotherapy-induced peripheral neuropathy (CIPN). Mechanosensitivity was compared between the different experimental groups. Von Frey test filament (4 g) was pressed to the plantar surface of the hindpaw until the filament just bent. The percent positive response (i.e. paw withdrawal) was recorded for Control, Paclitaxel, Oxaliplatin, Paclitaxel MCT/LC/Curcumin/EGCG/SFN, and Oxaliplatin+MCT/LC/Curcumin/EGCG/SFN treated mice after a cumulative dose of 25 mg/kg of Paclitaxel and 40 mg/kg of Oxaliplatin. Mechanosensitivity was reduced with Paclitaxel [A] and increased with Oxaliplatin [B] treatment, and addition of MCT/LC/Curcumin/EGCG/SFN resulted in a statistically significant attenuation of the chemotherapy treatment neuropathy. ***, p<0.001, compared to control, one-way ANOVA. ##, p<0.01, t-test, compared to Paclitaxel, ###, p<0.001, ##, p<0.05, compared to Oxaliplatin, one-way ANOVA.

Figure 13:
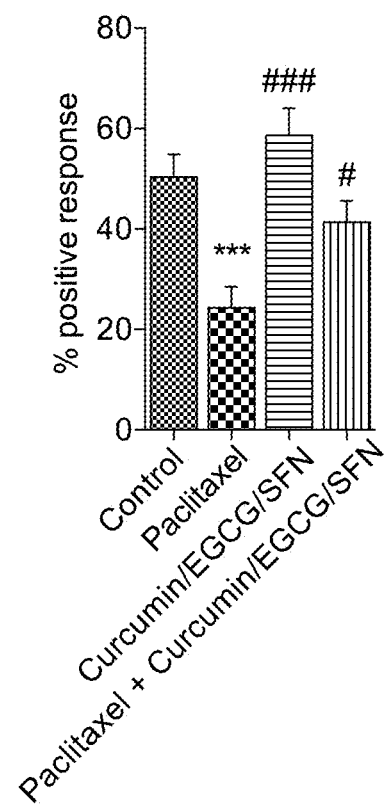

FIG. 13: Curcumin/EGCG/SFN inhibits chemotherapy-induced peripheral neuropathy (CIPN). Mechanosensitivity was compared between the different experimental groups. Von Frey test filament (4 g) was pressed to the plantar surface of the hindpaw until the filament just bent. The percent positive response (i.e. paw withdrawal) was recorded for Control, Paclitaxel, Paclitaxel+Curcumin/EGCG/SFN treated mice after a cumulative dose of 25 mg/kg of Paclitaxel. Mechanosensitivity was significantly reduced with Paclitaxel treatment, and addition of Curcumin/EGCG/SFN resulted in a statistically significant attenuation of the chemotherapy treatment neuropathy. ***, p<0.001, compared to control, one-way ANOVA. ###, p<0.001, #, p<0.05, one way ANOVA, compared to Paclitaxel.

Figure 14:
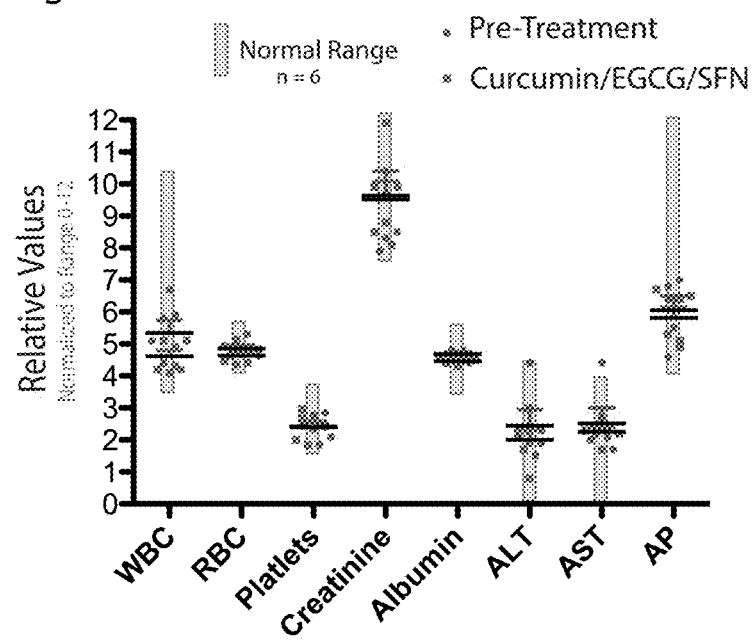

FIG. 14: Human safety profile of Curcumin/EGCG/SFN. Six patients [mean age=39, range 21-62 years of age] took Curcumin/EGCG/SFN for approximately 2 months [mean 73 days]. Blood samples were taken prior to beginning treatment and 2 months later. Complete Blood Count [CBC] and Complete Metabolic Profile [CMP] were analyzed from the blood samples. All data indicative of blood cell and organ health fell within normal ranges. Conclusion: Curcumin/EGCG/SFN is safe with no noted adverse effects on blood or major organ function.

WBC—white blood cells, cells responsible for immune function

RBC—red blood cells, oxygen carrying cells

Platelets—cell responsible for blood clotting

Creatinine—indicator of kidney function

Albumin—indicator of liver and kidney function

ALT—Alanine Aminotransferase—measure of liver health/damage

AST—Aspartate Aminotransferase—measure of heart and/or liver health/damage

AP—Alkaline Phosphatase—measure of liver health/damage

Dosage: Curcumin [2.6 g/day], EGCG [0.426 g/day], SFN [19 mg/day].

DETAILED DESCRIPTION OF THE INVENTION

Dietary Intervention for Neurological Disorders

The ketogenic diet has been used for over 80 years principally as a method to control seizures in pediatric patients. However, recently there is evidence from both uncontrolled clinical trials and preclinical models that the ketogenic diet may be a potential treatment for a number of neurological disorders and that it's broad neuroprotective properties may be mediated by altering cellular metabolism allowing neural cells to resist metabolic changes and upregulate protective mechanisms via antioxidant and anti-inflammatory mechanisms[1,2]. The use of dietary therapies to treat neurological disorders dates back to the time of Hippocrates but in the modern age it was the observation by two physicians at Harvard Medical School in the 1920s who noted that the seizure reducing effects of fasting could be replicated by abolishing carbohydrate intake. From this observation the ketogenic diet was developed and involved a high-fat [90% of caloric intake] and very low carbohydrate [less than 5%] diet that resulted in an increase in serum ketone bodies, and reduction in glucose levels that mimicked the effects of fasting or starvation. Today there exist several variations on the classic ketogenic diet, such as the modified Atkins diet and the medium chain triglyceride [MCT] diet, which are aimed at easing the severe carbohydrate restriction and excessive fat consumption posed by the traditional ketogenic diet and increasing compliance by making the approach more palatable and healthy. Aside from reducing seizure activity in children and adults the ketogenic diet, and similar variations, have shown various degrees of preclinical and clinical efficacy in a number of neurological disorders including; Alzheimer's disease, Parkinson's disease, ischemia, depression, migraine, ALS, brain injury, pain and inflammation[2-6]. One of the more interesting applications for the ketogenic diet has been as a therapy for cancer.

Ketogenic Diet [KD] and Cancer

Most solid tissue tumor populations rely on glycolysis for energy production. Due to their high rate of proliferation tumor cells divert nutrients into macromolecular pathways and the synthesis of new biomass, while simultaneously maintaining ATP levels[7,8]. This creates a dependency on high levels of glucose for optimal tumor cell function. The increased glucose flux promotes cell cycle progression and angiogenesis, and inhibits apoptosis[9,10]. However, in spite of the advantages this may have for the tumor cell it may also present an opportunity for therapeutic intervention. The shift towards glycolysis in cancer cells is known as the Warburg effect, described in the 1920s by its originator Otto Warburg who believed the shift from respiration to fermentation was a triggering event for cancer formation[8]. Therapies designed to target aerobic glycolysis have shown promising results by inhibiting glycolysis, blocking the pentose phosphate pathway and application of ketogenic diets[9,10,11,12]. While most malignant cancers are dependent on glucose for their survival and growth, they are also largely unable to metabolize ketone bodies for energy production due partially to compromised oxidative phosphorylation[13-15] and increased mitochondrial mutations[12]. Hence, application of a ketogenic diet that reduces glucose levels and generates ketone bodies can provide an energy substrate for non-tumor cells (i.e. brain and heart) while at the same time restricting energy supply for tumor cells as a result of metabolic inflexibility[9,15]. The focus of a ketogenic diet is to induce ketosis by limiting carbohydrate intake and increasing protein and principally fat intake. In this situation the liver processes fatty acids, generating ketone bodies that can be used in place of glucose to drive cellular energy production. The use of this approach in cancer is relatively new and was sparked by a landmark case report published in 1995 by Nebeling and coworkers who used the diet to treat two children with advanced pediatric astrocytoma that was progressing after standard of care treatments[16,17]. Both children exhibited significant recovery and were alive and well five years after they began dietary therapy. Since this time a number of preclinical studies have demonstrated the efficacy in reducing tumor growth in different cancers such as brain and prostate[18,19]. Positive results were reported on a patient with grade IV glioma while on a ketogenic diet and clinical trials have been completed or are underway to assess the efficacy of this approach for advanced cancers[20,21]. Multiple researchers have demonstrated that the use of a KD causes a reduction in blood glucose, an elevation in blood ketones and extends life in mouse models of malignant tumors[14,21]

Dietary Intervention for Managing the Negative Side Effects of Chemotherapy

Although chemotherapy can extend survival in cancer patients, many cancer treatments cause significant injury to normal cells. Not only can this lead to a reduction in the patient's quality of life, while undergoing treatment, and potentially long-term health problems and disabilities but can also be dose limiting, which may ultimately influence treatment efficacy. Based on data from calorie restriction experiments, which have been shown to increase lifespan, enhanced stress resistance, attenuate oxidative damage and delay age associated diseases, Longo and colleagues implemented a short term fasting regime in animals and humans who were undergoing chemotherapy. They found that fasting was able to protect against many of the cytotoxic effects without compromising the ability of the treatment to reduce tumor proliferation and burden[22-26]. In a case series of 10 patients, Raffaghello and colleagues reported that fasting was well tolerated with self-reported reductions in multiple chemotherapy-induced side effects including numbness, tingling and motor neuropathy[23]. These results fit with previous reports noting that intermittent fasting improves glucose metabolism and increased neuronal resistance to excitotoxic stress[27]. As the KD, fasting and caloric restriction elicit many overlapping physiological changes [reduced glucose, increased ketones, reduction in IGF1 and insulin, alter mTOR and PIK3 signaling] it is likely that the KD may have similar effects in attenuating chemotherapy related toxicities as has been seen with short-term fasting.

Development of a Modified Ketogenic Diet

While the KD may have application for treating cancer, chemotherapy induced side effects and other neurological disorders, it is difficult to implement due to its stringent nature (90-95% fat). The two key physiological changes that occur when on a ketogenic diet is a lowering of glucose levels and an elevation of circulating ketones. We have developed a protocol that mimics the key physiological effects of a ketogenic diet. This diet involves consuming a low carbohydrate diet [10-20% range] so as to reduce glucose levels and consuming medium chain triglycerides [MCT], which elevate blood ketone levels. In addition, other methods exist to mimic the physiological effects of the Ketogenic diet and include the use of Ketone bodies [KB] and Ketone body esters [KE] such as R,S-1,3-butanediol acetoacetate diester, 1.3-butanediol and R-3-hydroxybutyrate-R-1,3-butanediol monoester to mention a few[28,29]. Oral delivery of these compounds cause a rise in blood ketone levels and a corresponding reduction in glucose, mimicking the multitude of effects of the classical Ketogenic Diet. Hence, the classic Ketogenic Diet can be replicated in many ways including a supplemented high fat low carbohydrate diet and/or the use of Ketone bodies and Ketone esters.

Natural Products

The second aspect of our approach involves the simultaneous application of 3 natural products: [1] curcumin, [2] sulforaphane, from broccoli sprout powder [BSP] and [3] a green tea catachin, epigallocatechin 3-gallate [EGCG] and have demonstrated anti-inflammatory and anti-oxidant properties, are non-toxic and have a documented safety profile[30-32].

1. Epigallocatechin 3-Gallate [EGCG]

Epigallocatechin-3-gallate is the most abundant catechin in green tea, which is the most consumed beverage worldwide after water. Polyphenols derived from green tea are well-known to have anti-inflammatory, antioxidant properties and have been demonstrated to play a role in inhibit tumor cell proliferation in multiple animal models of cancer. These effects are due to the ability of EGCG to decrease cell proliferation, increase apoptosis, suppress angiogenesis and affect a number of molecular pathways that contribute to the development of resistance and cancer robustness. These actions are seen at micromolar concentrations that can be achieved by oral ingestion of ECGC[33].

Neuroprotective Effects of EGCG

EGCG has demonstrated neuroprotective effects in many settings in vitro and in vivo. EGCG protects neurons from a variety of toxic agents[34-36]. It directly functions as a reactive oxygen species (ROS) scavenger and activates antioxidant enzymes. EGCG additionally decreased activation of neuronal apoptosis and reduced activating inflammatory signals to microglial cells[35,37,38]. EGCG activates Protein Kinase C gamma signalling which reduces apoptotic signals and protects against cytoskeletal degradation[39,40]. Additionally EGCG appears to stimulate neurite outgrowth, which may promote the regain of lost neurologic function[40]. EGCG is currently in clinical trials for neuroprotective effects in Alzheimer's, Multiple Sclerosis, Diabetes, and Parkinson's Disease.

Safety of EGCG

Oral doses as high as 500 mg/kg in rodents were found to have no genotoxic or short term toxicity, a dosage that is significantly higher than that proposed for humans[41-43]. Similarly, no adverse events or toxicity was seen when 500 mg/kg/day was delivered to pre-fed dogs in a divided dosage for 13 weeks[42]. Epidemiological data indicates that nearly a quarter of Japanese consume more than 10 cups of green tea a day, which is the equivalent of approximately 1000 mg of EGCG daily[44].

2. Curcumin

Curcumin is the active component of the dietary spice turmeric [the yellow pigment in curry powder] and has been used in traditional medicine for the treatment of inflammation and disease. The biological functions of curcumin are diverse and range from having anti-tumor, anti-oxidative, anti-viral, anti-amyloid, anti-bacterial and anti-hepatotoxic activities[45]. In the past 20 years hundreds of research papers have been published investigating the underlying mechanisms of these effects. The mechanisms are diverse and appear to occur via regulation of a number of molecular targets[46].

Neuroprotective Effects of Curcumin

Curcumin has been evaluated using many neuropathy models and specifically decreased oxaliplatin induced demyelination[47] and prevented cisplatin-mediated suppression of neurite outgrowth without diminishing anticancer effects[48]. Curcumin has demonstrated reduction of neuropathic pain in clinical trials of patients with sciatica and carpal tunnel syndrome[49]. It has been demonstrated to alleviate neuropathic pain via actions on the monoamine system[50] and reduce diabetic neuropathy through reduction of oxidative stress[51] and inhibition of NF-kappa b activation of TNF-alpha and IL-6[52] in animal models. This anti-inflammatory effect is also observed in ischemia models to be mediated through NF-KB signaling[53]. Currently the effect of curcumin on neuropathology is in human trials for Alzheimer's, Optic Neuropathy, and spinal cord injury.

Safety of Curcumin

The average consumption of curcumin in the typical Indian diet is about 100 mg curcumin a day[54]. Several toxicity studies in animals at high doses has shown it to be safe in preclinical models such as rats, guinea pigs and monkeys[55][56]. Clinical studies have shown the safety of curcumin up to 8000 mg/day for up to 3 months[57]. Lao and colleagues conducted another study in healthy subjects with doses escalating from 5000 to 12,000 mg/day, with no significant adverse side effects[58]. Several clinical studies (mostly single-arm phase II) have indicated the effectiveness of curcumin in chronic inflammation, pre-malignant and malignant lesions and AIDS[59][60][61][62].

3. Sulforaphane

Many of the anticancer effects of cruciferous vegetables have been attributed to isothiocyanates [ITC], which are formed by hydrolysis of their precursor parent molecule glucosinolates. One of the most studied cruciferous vegetable ITCs is sulforaphane [SFN] whose precursor glucoraphanin [GRP] is abundant in broccoli, cauliflower and cabbage, with the highest concentration being found in broccoli sprouts. Hydrolysis of GRP requires the activity of myrosinase enzymes that are present in the vegetables themselves and in microflora of the colon[63]. SFN is rapidly absorbed with a 80% bioavailability and attains peak plasma levels within 2 hours and is characterized by a long terminal elimination phase[64,65]. A great deal of research has gone into studying SFN's ability to simultaneously modulate multiple cellular targets related to cancer development. These includes its ability to protect DNA by altering carcinogen-metabolizing enzymes and blocking mutagens, inhibiting proliferation, inducing apoptosis, inhibiting angiogenesis and inhibiting histone deacetylase[66]. SFN has been shown to inhibit malignant progression of lung adenomas[67] and to selectively target benign hyperplasia cells and cancerous cells while leaving normal prostate cells unaffected[68]. Importantly, SFN is a potent inhibitor of Phase 1 enzymes, stimulator of Phase 2 enzymes [via NrF2], can reduce oxidative stress and inhibit NF-kB[69-71]. In addition, SFN is a potent HDAC inhibitor[66,72,73].

Neuroprotective Effects of Sulforaphane

Sulforaphane, like other isothiocyanates, has been shown to raise tissue glutathione levels, augmenting the cellular antioxidant defenses inherent within virtually all cells[74]. Additional animal and human studies have shown induction of numerous Phase II enzymes (via the Nrf2 pathway mentioned above), including superoxide dismutase, catalase, NAD(P)H:quinine oxidoreductase 1, glutathione peroxidase, glutathione reductase and glutathione-s-transferase[75]. A randomized, double-blind clinical trial also demonstrated sulforaphane's ability to reduce oxidative stress in type-2 diabetes[76]. Sulforaphane has been shown to protect neural mitochondria by activating Nrf2[77] and reduce neuroinflammation by inhibiting NF-KB[78]. Furthermore, sulforaphane has been studied mostly for its anti-carcinogenic effects, Ping et al examined its antioxidative and neuroprotective effects against hypoxic-ischemic injury in a neonatal rat mode[79]. It was observed that sulforaphane treatment increased the expression of the Nrf2 antioxidative transcription factor in the brain. They also found that sulforaphane reduced infarct ratio at 24 hours after hypoxic ischemia, and significantly decreased the number of apoptotic cells.

Safety of Sulforaphane

Broccoli sprouts are widely consumed as a food all over the world, without any reported adverse effects. Research studies performed in humans have not demonstrated any significant adverse effects of administration of sulforaphane or sulforaphane-enriched dietary origin items such as broccoli sprouts. Increasing evidence supports the view that sulforaphane is considered to be of low toxicity.

An oral intake of 68 grams of broccoli sprouts is demonstrated to provide a safe non-toxic dose [100 mg] of SFN, that has proven therapeutic in cancer models[80]. In another study, 81 patients with type 2 diabetes were treated for 4 weeks with a dose of up to 10 grams of broccoli sprout powder with no reported side effects[76].

Proliferative Disorder

The current invention is directed to manage negative side effects of therapeutic regimens used to treat proliferative diseases (such as cancer). The negative side effects of the proliferative disorders that can be treated with the treatment of current invention include, but are not limited to, Acute Lymphoblastic Leukemia, Acute Myeloid Leukemia, Adrenocortical Carcinoma, AIDS-Related Cancers, AIDS-Related Lymphoma, Anal Cancer, Appendix Cancer, Astrocytoma, Cerebellar Astrocytoma, Basal Cell Carcinoma, Bile Duct Cancer, Extrahepatic Bladder Cancer, Bladder Cancer, Bone Cancer, Osteosarcoma and Malignant Fibrous Histiocytoma, Embryonal Tumors, Cerebral Astrocytoma, Ependymoblastoma, Medulloblastoma, Medulloepithelioma, Pineal Parenchymal Tumors of Intermediate Differentiation, Supratentorial Primitive Neuroectodermal Tumors and Pineoblastoma, Visual Pathway and Hypothalamic cancer, Brain and Spinal Cord Tumors, Breast Cancer, Bronchial Tumors, Burkitt Lymphoma, Carcinoid Tumor, Gastrointestinal Cancer, Carcinoma of Head and Neck, Central Nervous System Lymphoma, Cervical Cancer, Chronic Lymphocytic Leukemia, Chronic Myelogenous Leukemia, Chronic Myeloproliferative Disorders, Colorectal Cancer, Cutaneous T-Cell Lymphoma, Endometrial Cancer, Ependymoblastoma, Ependymoma, Esophageal Cancer, Ewing Family of Tumors, Extracranial Germ Cell Tumor, Extrahepatic Bile Duct Cancer, Eye Cancer, Intraocular Melanoma, Retinoblastoma, Gallbladder Cancer, Gastric (Stomach) Cancer, Gastrointestinal Carcinoid Tumor, Gastrointestinal Stromal Tumor (GIST), Extracranial Germ Cell Tumor, Germ Cell Tumor, Extragonadal Germ Cell Tumor, Ovarian Cancer, Gestational Trophoblastic Tumor, Hairy Cell Leukemia, Head and Neck Cancer, Hepatocellular (Liver) Cancer, Hepatocellular (Liver) Cancer, Hodgkin Lymphoma, Hypopharyngeal Cancer, Intraocular Melanoma Islet Cell Tumors (Endocrine Pancreas), Kaposi Sarcoma, Kidney (Renal Cell) Cancer, Kidney Cancer, Laryngeal Cancer, Chronic Lymphocytic Leukemia, Chronic Leukemia, Myelogenous Leukemia, Lip and Oral Cavity Cancer, Lung Cancer, Non-Small Cell Lung Cancer, Small Cell Lymphoma, Cutaneous T-Cell Lymphoma, Non-Hodgkin Lymphoma, Macroglobulinemia, Waldenström, Malignant Fibrous Histiocytoma of Bone and Osteosarcoma, Medulloblastoma, Medulloepithelioma, Melanoma, Intraocular Merkel Cell Carcinoma, Mesothelioma, Metastatic Squamous Neck Cancer with Occult Primary, Mouth Cancer, Multiple Endocrine Neoplasia Syndrome, Multiple Myeloma/Plasma Cell Neoplasm, Mycosis Fungoides, Myelodysplastic Syndromes, Myelodysplastic/Myeloproliferative Diseases, Myelogenous Leukemia, Multiple, Myeloproliferative Disorders, Nasal Cavity and Paranasal Sinus Cancer, Nasopharyngeal Cancer, Neuroblastoma, Non-Small Cell Lung Cancer, Oral Cancer, Oral Cavity Cancer, Lip and Oropharyngeal Cancer, Osteosarcoma and Malignant Fibrous Histiocytoma of Bone, Ovarian Epithelial Cancer, Ovarian Germ Cell Tumor, Ovarian Low Malignant Potential Tumor, Pancreatic Cancer, Pancreatic Cancer, Islet Cell Tumors, Papillomatosis, Paranasal Sinus and Nasal Cavity Cancer, Parathyroid Cancer, Penile Cancer, Pharyngeal Cancer, Pheochromocytoma, Pineal Parenchymal Tumors of Intermediate Differentiation, Pineoblastoma and Supratentorial Primitive Neuroectodermal Tumors, Pituitary Tumor, Plasma Cell Neoplasm/Multiple Myeloma, Pleuropulmonary Blastoma, Primary Central Nervous System Lymphoma, Prostate Cancer, Rectal Cancer, Renal Cell (Kidney) Cancer, Renal Pelvis and Ureter Cancer, Transitional Cell Cancer, Respiratory Tract Carcinoma Involving the NUT Gene on Chromosome 15, Retinoblastoma, Rhabdomyosarcoma, Salivary Gland Cancer, Sarcoma, Ewing Family of Tumors Sarcoma, Kaposi Sarcoma, Soft Tissue Sarcoma, Uterine Sézary Syndrome, Skin Cancer (Nonmelanoma), Skin Carcinoma, Merkel Cell, Small Cell Lung Cancer, Small Intestine Cancer, Squamous Cell Carcinoma, Squamous Neck Cancer with Occult Primary Cancer, Supratentorial Primitive Neuroectodermal Tumors, T-Cell Lymphoma, Mycosis Fungoides and Sézary Syndrome, Testicular Cancer, Throat Cancer, Thymoma and Thymic Carcinoma, Thyroid Cancer, Transitional Cell Cancer of the Renal Pelvis and Ureter, Gestational Trophoblastic Tumor, Carcinoma of Unknown Primary Site, Urethral Cancer, Uterine Cancer, Endometrial Uterine Sarcoma, Vaginal Cancer, Vulvar Cancer, Waldenström Macroglobulinemia, and Wilms Tumor.

Anti-Cancer Treatments

The therapeutic protocols to treat proliferative disorders include, but are not limited to, administering one or more of: Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Adriamycin (Doxorubicin Hydrochloride), Adrucil (Fluorouracil), Afinitor (Everolimus), Aldara (Imiquimod), Aldesleukin, Alemtuzumab, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Arimidex (Anastrozole), Aromasin (Exemestane), Arranon (Nelarabine), Arsenic Trioxide, Arzerra (Ofatumumab), Asparaginase Erwinia chrysanthemi, Avastin (Bevacizumab), Axitinib, Azacitidine, BEACOPP, Bendamustine Hydrochloride, BEP, Bevacizumab, Bexarotene, Bexxar (Tositumomab and I 131 Iodine Tositumomab), Bleomycin, Bortezomib, Bosulif (Bosutinib), Bosutinib, Brentuximab Vedotin, Cabazitaxel, Cabozantinib-S-Malate, CAF, Campath (Alemtuzumab), Camptosar (Irinotecan, ydrochloride), Capecitabine, CAPDX, Carboplatin, CARBOPLATIN-TAXOL, Carfilzomib, CeeNU (Lomustine), Cerubidine (Daunorubicin Hydrochloride), Cervarix (Recombinant HPV Bivalent Vaccine), Cetuximab, Chlorambucil, CHLORAMBUCIL-PREDNISONE, CHOP, Cisplatin, Clafen (Cyclophosphamide), Clofarabine, Clofarex (Clofarabine), Clolar (Clofarabine), CMF, Cometriq (Cabozantinib-S-Malate), COPP, Cosmegen (Dactinomycin), Crizotinib, CVP (COP), Cyclophosphamide, Cyfos (Ifosfamide), Cytarabine, Cytarabine, Liposomal, Cytosar-U (Cytarabine), Cytoxan (Cyclophosphamide), Dacarbazine, Dacogen, (Decitabine), Dactinomycin, Dasatinib, Daunorubicin Hydrochloride, Decitabine, Degarelix, Denileukin, iftitox, Denosumab, DepoCyt (Liposomal Cytarabine), DepoFoam (Liposomal Cytarabine), Dexrazoxane hydrochloride, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase Erwinia chrysanthemi), Etopophos (Etoposide Phosphate), Etoposide, Etoposide Phosphate, Evacet (Doxorubicin Hydrochloride Liposome), Everolimus, Evista (Raloxifene Hydrochloride), Exemestane, Fareston (Toremifene), Faslodex (Fulvestrant), FEC, Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), FOLFIRI, FOLFIRI-BEVACIZUMAB, FOLFIRINOX, FOLFOX, Folotyn (Pralatrexate), FU-LV, Fulvestrant, Gardasil (Recombinant HPV Quadrivalent Vaccine), Gefitinib, Gemcitabine Hydrochloride, GEMCITABINE-CISPLATIN, Gemtuzumab Ozogamicin, Gemzar (Gemcitabine, ydrochloride), Gleevec (Imatinib Mesylate), Glucarpidase, Halaven (Eribulin Mesylate), Herceptin (Trastuzumab), HPV Bivalent Vaccine, Recombinant, HPV Quadrivalent Vaccine (Recombinant), Hycamtin (Topotecan Hydrochloride), Ibritumomab Tiuxetan, ICE, Iclusig (Ponatinib Hydrochloride), Ifex (Ifosfamide), Ifosfamide, Ifosfamidum (Ifosfamide), Imatinib Mesylate, Imiquimod, Inlyta (Axitinib), Ipilimumab, Iressa (Gefitinib), Irinotecan Hydrochloride, Istodax (Rom idepsin), Ixabepilone, Ixempra (Ixabepilone), Jakafi (Ruxolitinib Phosphate), Jevtana (Cabazitaxel), Keoxifene (Raloxifene Hydrochloride), Kepivance (Palifermin), Kyprolis (Carfilzomib), Lapatinib Ditosylate, Lenalidomide, Letrozole, Leucovorin Calcium, Leukeran (Chlorambucil), Leuprolide Acetate, Levulan (Aminolevulinic (Acid), Linfolizin (Chlorambucil), LipoDox (Doxorubicin Hydrochloride Liposome), Liposomal Cytarabine, Lomustine, Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Marqibo (Vincristine Sulfate Liposome), Matulane (Procarbazine Hydrochloride), Mechlorethamine Hydrochloride, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitozytrex (Mitomycin C), MOPP, Mozobil (Plerixafor), Mustargen (Mechlorethamine hydrochloride), Mutamycin (Mitomycin C), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Nelarabine, Neosar (Cyclophosphamide), Neupogen (Filgrastim), Nexavar (Sorafenib Tosylate), Nilotinib, Nolvadex (Tamoxifen Citrate), Nplate (Romiplostim), Ofatumumab, Omacetaxine Mepesuccinate, Oncaspar (Pegaspargase), Ontak (Denileukin Diftitox), Oxaliplatin, Paclitaxel, Paclitaxel Albumin-stabilized Nanoparticle Formulation, Paliferm in, Palonosetron Hydrochloride, Panitumumab, Paraplat (Carboplatin), Paraplatin (Carboplatin), Pazopanib Hydrochloride, Pegaspargase, Pemetrexed Disodium, Perjeta (Pertuzumab), Pertuzumab, Platinol (Cisplatin), Platinol-AQ (Cisplatin), Plerixafor, Ponatinib Hydrochloride, Pralatrexate, Prednisone, Procarbazine Hydrochloride, Proleukin (Aldesleukin), Prolia (Denosumab), Promacta (Eltrombopag Olamine), Provenge (Sipuleucel-T), Raloxifene hydrochloride, Rasburicase, R-CHOP, R-CVP, Recombinant HPV Bivalent Vaccine, Recombinant HPV, Quadrivalent Vaccine, Regorafenib, Revlimid (Lenalidomide), Rheumatrex (Methotrexate), Rituxan (Rituximab), Rituximab, Romidepsin, Rom iplostim, Rubidomycin (Daunorubicin Hydrochloride), Ruxolitinib Phosphate, Sclerosol Intrapleural Aerosol (Talc), Sipuleucel-T, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Synovir (Thalidomide), Synribo (Omacetaxine Mepesuccinate), Talc, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Toposar (Etoposide), Topotecan Hydrochloride, Toremifene, Torisel (Temsirolimus), Tositumomab and I 131 Iodine Tositumomab, Totect (Dexrazoxane Hydrochloride), Trastuzumab, Treanda (Bendamustine Hydrochloride), Trisenox (Arsenic Trioxide), Tykerb (Lapatinib Ditosylate), Vandetanib, VAMP, Vectibix (Panitumumab), VeIP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, Vismodegib, Voraxaze (Glucarpidase), Vorinostat, Votrient (Pazopanib Hydrochloride), Wellcovorin (Leucovorin Calcium), Xalkori (Crizotinib), Xeloda (Capecitabine), XELOX, Xgeva (Denosumab), Xtandi (Enzalutamide), Yervoy (Ipilimumab), Zaltrap (Ziv-Aflibercept), Zelboraf (Vemurafenib), Zevalin (Ibritumomab Tiuxetan), Zinecard (Dexrazoxane Hydrochloride), Ziv-Aflibercept, Zoledronic Acid, Zolinza (Vorinostat), Zometa (Zoledronic Acid), and Zytiga (Abiraterone Acetate).

Anti-Cancer Treatments' Negative Side Effects

The negative sides effects of therapeutic protocols implemented to treat proliferative disorders include, but are not limited to: nausea, fatigue, dizziness, shortness in breath, pain, sores in mouth and throat, diarrhea, nausea, vomiting, constipation, blood disorders such anemia, leukopenia, thrombocytopenia (involving abnormal levels of red blood cells, white blood cells or platelets respectively), change in thinking and memory, sexual and reproductive ailment, appetite loss, hair loss, nervous system effects resulting in altered cognition and in one or more of the following nerve- or muscle-related symptoms including tingling, burning, weakness or numbness in the hands and/or feet (peripheral neuropathy), weak, sore, tired, or achy muscles, loss of balance, shaking or trembling, stiff neck, headache, visual problems, walking problems, difficulty hearing, clumsiness. Nervous system can also be affected through the targeting of neural stem cells. Targeting normal stem cells represents a severe limitation on the dosage of chemotherapeutics agents. By rendering normal stem cells resistant to chemotoxicity, the invention provides a novel approach to effectively mitigate negative side effects of chemotherapy with critical functional implications for the subjects treated with conventional chemotherapeutics agents.

EXAMPLES

1. The Proposed Method [MCT/LC/Curcumin/EGCG/SFN] is Safe and has No Sign of Toxicity.

Figure 1:
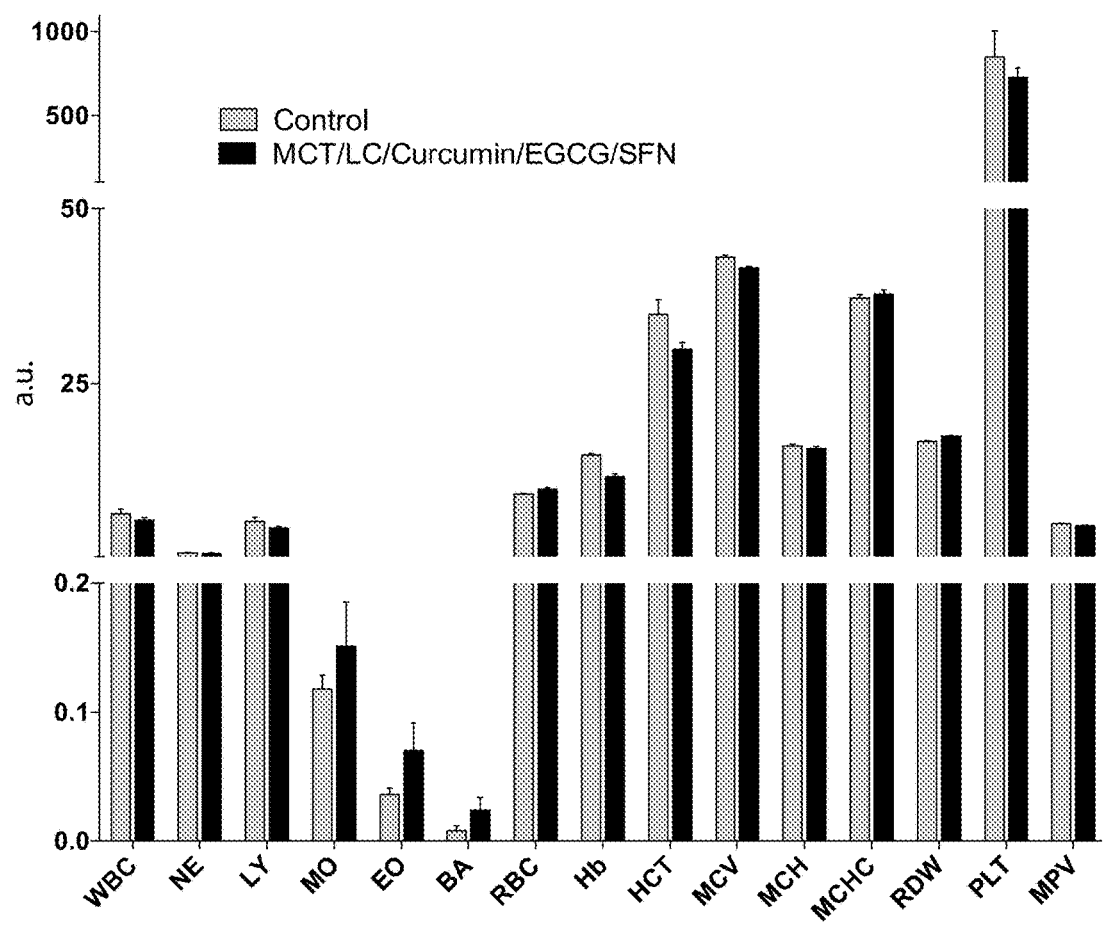
FIG. 1: Toxicity profile of our treatment. Toxicity was assessed after 4 weeks of treatment via comparing values of a full Complete Blood Count [CBC]. No difference was observed between the experimental group and controls with all values being in normal range. White blood cells [WBC], neutrophils [NE], lymphocytes [LY], monocytes [MO], eosinophils [EO], basophils [BA], red blood cells [RBC], hemoglobin [Hb], hematocrit [HCT], mean corpuscular volume [MCV], mean corpuscular hemoglobin [MCH], mean corpuscular hemoglobin concentration [MCHC], red blood cell distribution width [RDW], platelet [PLT], mean platelet volume [MPV].

Mice were fed with a control diet or the MCT/LC/Curcumin/EGCG/SFN diet. After two weeks of treatments, blood was collected via retro-orbital puncture and blood samples were processed for Complete Blood Count (CBC). CBC is used to evaluate over health and detect a wide range of disorders, which can be related to treatment toxicity. Abnormal increase or decrease of the components measured in the CBC (including white blood cells [WBC], neutrophils [NE], lymphocytes [LY], monocytes [MO], eosinophils [EO], basophils [BA], red blood cells [RBC], hemoglobin [Hb], hematocrit [HCT], mean corpuscular volume [MCV], mean corpuscular hemoglobin [MCH], mean corpuscular hemoglobin concentration [MCHC], red blood cell distribution width [RDW], platelet [PLT], mean platelet volume [MPV]) may indicate underlying treatment toxicity. FIG. 1 reveals no statistically significant differences in the different measured blood parameters between control and MCT/LC/Curcumin/EGCG/SFN fed animals. The safety of MCT/LC/Curcumin/EGCG/SFN treatment was further assessed by measuring the effect of the treatment on the mass of organs. MCT/LC/Curcumin/EGCG/SFN was provided for 4 weeks and the organs (liver and kidneys) were isolated and their mass were determined. The results of FIG. 2 show no difference in organs mass between the experimental groups. Together, these results support the conclusion that the treatment MCT/LC/Curcumin/EGCG/SFN is safe and has no noted toxic side effects.

Treatments composition is as follow: [1] Control=55% carbohydrates, 30% proteins, 15% fat. [2] MCT/LC/Curcumin/EGCG/SFN=10-20% carbohydrates, 50-60% fat (about half coming from MCT), 30% Proteins+Curcumin [1200 mg/kg of body weight], EGCG [1200 mg/kg of body weight]), SFN [25 mg/kg of body weight].

2. the Presented Invention [MCT/LC/Curcumin/EGCG/SFN] Prevents or Mitigates Chemotherapy-Induced Anemia.

Animals were treated with three different chemotherapy agents inducing anemia (20 mg/kg TMZ, 100 mg/kg 5-FU, 40 mg/kg oxaliplatin). After two to four weeks of treatments blood was collected via retro-orbital puncture from the different experimental groups. Blood samples were processed for CBC. Results from FIGS. 3-5 show that the chemdrugs induced anemia as demonstrated by a decreased level of red blood cell count, hemoglobin and hematocrit. Importantly, MCT/LC/Curcumin/EGCG/SFN was able to prevent the chemo-induced anemia and maintained the level of red blood cell counts, hematocrit and hemoglobin to a level similar to control. Together these data demonstrate the ability of MCT/LC/Curcumin/EGCG/SFN to prevent anemia induced by chemotherapy treatments.

3. the Presented Invention [MCT/LC/Curcumin/EGCG/SFN] Prevents or Mitigates Chemotherapy-Induced Leukopenia.

Animals were treated with different chemotherapy agents inducing leukopenia (20 mg/kg TMZ, 100 mg/kg 5-FU). After two weeks of treatments blood was collected via retro-orbital puncture from the different experimental groups (control, MCT/LC/Curcumin/EGCG/SFN, TMZ, 5-FU, TMZ+MCT/LC/Curcumin/EGCG/SFN, and 5-FU+MCT/LC/Curcumin/EGCG/SFN). Blood samples were processed for CBC. FIGS. 6 and 7 indicate that both drugs induced leukopenia as demonstrated by a decreased level of white blood cell and neutrophil count and that combining these chemo drugs with MCT/LC/Curcumin/EGCG/SFN prevented or attenuated these negative side effects. These results establish the ability of MCT/LC/Curcumin/EGCG/SFN to prevent or inhibit leukopenia induced by chemotherapy treatments.

4. MCT/LC/Curcumin/EGCG/SFN Prevents Nephrotoxicity and Hepatotoxicity Related to Chemotherapy.

The mass of the liver and kidneys were quantified and compared between all experimental groups (control, MCT/LC/Curcumin/EGCG/SFN, Paclitaxel, and Paclitaxel+MCT/LC/Curcumin/EGCG/SFN) to establish the capability of MCT/LC/Curcumin/EGCG/SFN to inhibit the organ-targeted chemotoxicity [FIG. 8-9]. Mice were treated with paclitaxel alone [25 mg/kg] or in combination with MCT/LC/Curcumin/EGCG/SFN. After four weeks of treatments, the organs were harvested and their mass determined. Organs vulnerability was demonstrated by the decreased kidney mass [FIG. 8] and enlarged liver mass [FIG. 9] of animals treated with paclitaxel. Hence, these data teach us that MCT/LC/Curcumin/EGCG/SFN is able to protect organs such as kidneys and liver to toxicity related to chemotherapy.

5. MCT/LC/Curcumin/EGCG/SFN Demonstrates Neuroprotective Effect in the Context of Chemotherapy Treatment.

Mice were fed with control diet or MCT/LC/Curcumin/EGCG/SFN diet. Each dietary group was treated with TMZ [20 mg/kg] or 5-FU [100 mg/kg] for two weeks, after which point brains were harvested and the cells from the periventricular region were cultured at clonal density in the neurosphere assay during one passage (7-14 days) to quantify the sphere forming frequency indicating neural stem cells occurrence in the brains of animals treated with the different treatments. FIG. 10A shows that both chemotherapy agents target neural stem cells as demonstrated by decreased number of sphere forming cells in TMZ and 5-FU treated groups. MCT/LC/Curcumin/EGCG/SFN mitigated this diminution when combined with TMZ. Importantly, when combined with 5-FU, MCT/LC/Curcumin/EGCG/SFN completely prevented the negative effect of the chemo treatment and maintained level of neural stem cell activity similar to controls.

A cohort of animals received three injections of BrdU [50 mg/kg] over a 72-hour time period before to be euthanized. Brains were removed, fixed, sectioned and BrdU antibodies used to identify cells that were in S-phase during the 72 hour injection period. The number of BrdU-immunoreactive cells were enumerate in the brains (subventricular area and hippocampus) of animals from the different groups (control, MCT/LC/Curcumin/EGCG/SFN, 5-FU, and 5-FU+MCT/LC/Curcumin/EGCG/SFN). FIGS. 10B-E reveal that relative to controls, 5-FU treated animals exhibit less number of proliferating neural stem cells. Importantly, the combination group 5-FU+MCT/LC/Curcumin/EGCG/SFN shows level of proliferation similar to controls. These data indicate that the MCT/LC/Curcumin/EGCG/SFN treatment is able to prevent neurotoxicity and protect the endogenous neural stem cells from the negative effects of chemotherapy.

Peripheral neuropathy is a common side effect of several chemotherapies, including but not limited to taxanes and platinums (such as paclitaxel and oxaliplatin). Neuropathy is often the dose limiting toxicity of these agents and can devastatingly affect the patient due to diminished fine motor skills and pain in the hands and feet that diminishes the ability to exercise and interact in normal life. Clinically significant neuropathy occurs in 40% of patients and >10% will persist past a year causing permanent effects on quality of life. Perhaps more devastating, patients often have to discontinue effective treatment due to the development of these symptoms. We used two models of CIPN using cold allodynia [FIG. 11] and mechanosensitivity [FIG. 12] assays. Cold allodynia assay was performed after cumulative dose of 25 mg/kg of paclitaxel and 40 mg/kg of oxaliplatin. The assay consists of applying one drop of acetone to the plantar surface of the hindpaw using a 1 ml syringe. Mice were observed for 2.5 min after each acetone application. Spontaneous pain behavior (defined as shaking, flinching, or licking of the paw as well as holding the paw in an elevated position) that occurred within 2.5 min after acetone application was counted as a positive response. Spontaneous pain behavior that occurred within the first 15 s after acetone application was not counted, since most mice had some reaction to the initial application. The number of time exhibiting pain behavior was recorded and compared between the groups. Three to five trials were performed on each hind-paw with a 5 min interval between trials. These results demonstrate the ability of MCT/LC/Curcumin/EGCG/SFN to limit the level of paclitaxel and oxaliplatin-induced cold allodynia (indicative of peripheral neuropathy development).

Animals were also tested for neuropathic pain using the Von Frey Test where the sensitivity of the animals to mechanical stimulus is measured. Similar to the cold allodynia assay, the animals were tested after cumulative doses of 25 mg/kg paclitaxel and 40 mg/kg oxaliplatin. Von Frey test filament (4 g) was pressed to the plantar surface of the hindpaw until the filament just bent. The percent positive response (i.e. paw withdrawal) was recorded. FIG. 12 demonstrates the development of neuropathic pain by the animals treated with the chemotherapeutic agents. Importantly, hyper-mechanosensitivity was significantly reduced when the drugs were combined with MCT/LC/Curcumin/EGCG/SFN.

Altogether, these results demonstrate the ability of MCT/LC/Curcumin/EGCG/SFN to prevent or decrease neurotoxicity of chemotherapy.

6. Curcumin/EGCG/SFN Demonstrates Neuroprotective Effect in the Context of Chemotherapy Treatment.

Using a similar experimental paradigm as used in Example 5, FIG. 13 shows that the application of natural products [ie. the proposed method using Curcumin/EGCG/SFN) is able to significantly reduce and prevent the development of CIPN. Of note, this effect is observed in absence of implementing a low carbohydrate diet and MCT supplementation. Low level of glucose and high level of ketones are not necessary to observe the anti-CINP effect. Hence, patients can supplement their diet with the natural products detailed in this application and attenuate the negative side effects of chemotherapy.

7. Curcumin/EGCG/SFN is Safe.

Using IRB guidelines, patients were dose escalated beginning with 1.28 g, 1.22 g & 0.213 g of curcumin, broccoli sprout powder and EGCG, respectively. Blood tests to assess safety (Complete Blood Count [CBC] and Complete Metabolic Profile [CMP]) found no difference in the key indicators of safety in all patients when comparing levels before they began taking the supplements [data not shown]. Patients were dose escalated to 2.6 g, 2.4 g & 0.42 g of curcumin, broccoli sprout powder and EGCG, respectively. FIG. 14 summarized the clinical data from this patient population, clearly indicating that the combination of curcumin, broccoli sprout powder [containing SFN] and EGCG is safe.

8. Curcumin/EGCG/SFN can be Used with Other Methods that Increase Ketones.

Combining natural products and the classical Ketogenic diet can be used to prevent the negative side effects of chemotherapy. However, the classical Ketogenic diet can be difficult to implement. While a supplemental high fat low carbohydrate diet can be used in place of the classic Ketogenic Diet other methods to increase ketones, and thereby mimic the physiological effects of the classic Ketogenic Diet can be used as well. For instance, R,S-1,3-butanediol-diacetoacetate ester can be used to replicate the physiological and phenotypic effects of the classic Ketogenic Diet. R,S-1,3-butanediol-diacetoacetate ester is synthesized by transesterification of t-butylacetoacetate with R,S-1,3-butanediol and is a non-ionized, sodium-free, pH-neutral precursor of the ketone body acetoacetate (ACA). This Ketone ester consists of two ACA molecules esterified to one molecule of 1,3-butanediol, an organic alcohol commonly used as a solvent in food flavoring agents. When ingested, gastric esterases rapidly cleave the KE to release two ACA molecules, which are absorbed into circulation, rapidly elevating blood ketone concentration[81]. Hence, patients can be treated with R,S-1,3-butanediol-diacetoacetate ester to elicit the same effects as the classic Ketogenic diet and the supplemental high fat low carbohydrate diet. Other ketone bodies and ketone esters can be used as well, and in combination with natural products, such as curcumin, EGCG and broccoli sprout powder [containing SFN] to attenuate the negative side effects of chemotherapy.

REFERENCES

1 Gasior, M., Rogawski, M. A. & Hartman, A. L. Neuroprotective and disease-modifying effects of the ketogenic diet. *Behavioural Pharmacology* 17, 431-439 (2006).

2 Gano, L., Patel, M. & Rho, J. M. Ketogenic Diets, Mitochondria and Neurological Diseases. *Journal of lipid research*, jlr.R048975, doi:10.1194/jlr.R048975 (2014).

3 Gasior, M. M., Rogawski, M. A. M. & Hartman, A. L. A. Neuroprotective and disease-modifying effects of the ketogenic diet. *Behavioural Pharmacology* 17, 431-439, doi:10.1097/00008877-200609000-00009 (2006).

4 Ruskin, D. N., Kawamura, J., Masahito & Masino, S. A. Reduced Pain and Inflammation in Juvenile and Adult Rats Fed a Ketogenic Diet. *PLoS ONE* 4, e8349, doi: 10.1371/journal.pone.0008349 (2009).

5 Carl E Stafstrom, J. M. R. The Ketogenic Diet as a Treatment Paradigm for Diverse Neurological Disorders. *Frontiers in Pharmacology* 3, doi:10.3389/fphar.2012.00059 (2012).

6 Freeman, J. M., Kossoff, E. H. & Hartman, A. L. The ketogenic diet: one decade later. *PEDIATRICS* 119, 535-543, doi:10.1542/peds.2006-2447 (2007).

7 vander Heiden, M. G. Targeting cancer metabolism: a therapeutic window opens. *Nature Reviews Drug Discovery* 10, 671-684, doi:10.1038/nrd3504 (2011).

8 Vander Heiden, M. G., Cantley, L. C. & Thompson, C. B. Understanding the Warburg effect: the metabolic requirements of cell proliferation. *Science* 324, 1029-1033, doi: 10.1126/science.1160809 (2009).

9 Klement, R. J. & Kammerer, U. Is there a role for carbohydrate restriction in the treatment and prevention of cancer? *Nutrition & metabolism* 8, 75, doi:10.1186/1743-7075-8-75 (2011).

10 Tennant, D. A., Duran, R. V. & Gottlieb, E. Targeting metabolic transformation for cancer therapy. *Nature reviews Cancer*, doi:10.1038/nrc2817 (2010).

11 Koppenol, W. H., Bounds, P. L. & Dang, C. V. Otto Warburg's contributions to current concepts of cancer metabolism. *Nature reviews Cancer* 11, 325-337, doi:doi:10.1038/nrc3038 (2011).

12 Seyfried, T. N. & Shelton, L. M. Cancer as a metabolic disease. *Nutrition & metabolism* 7, 7, doi:10.1186/1743-7075-7-7 (2010).

13 Skinner, R., Trujillo, A., Ma, X. & Beierle, E. A. Ketone bodies inhibit the viability of human neuroblastoma cells. *Journal of pediatric surgery* 44, 212-216; discussion 216, doi:10.1016/j.jpedsurg.2008.10.042 (2009).

14 Zhou, W. et al. The calorically restricted ketogenic diet, an effective alternative therapy for malignant brain cancer. *Nutrition & metabolism* 4, 5, doi:10.1186/1743-7075-4-5 (2007).

15 Seyfried, T. N., Kiebish, M., Mukherjee, P. & Marsh, J. Targeting energy metabolism in brain cancer with calorically restricted ketogenic diets. *Epilepsia* 49 Suppl 8, 114-116, doi:10.1111/j.1528-1167.2008.01853.x (2008).

16 Nebeling, L. C., Miraldi, F., Shurin, S. B. & Lerner, E. Effects of a ketogenic diet on tumor metabolism and nutritional status in pediatric oncology patients: two case reports. *Journal of the American College of Nutrition* 14, 202-208 (1995).

17 Nebeling, L. C. & Lerner, E. Implementing a ketogenic diet based on medium-chain triglyceride oil in pediatric patients with cancer. *J Am Diet Assoc* 95, 693-697, doi:10.1016/50002-8223(95)00189-1 (1995).

18 Seyfried, T. N., Sanderson, T. M., El-Abbadi, M. M., McGowan, R. & Mukherjee, P. Role of glucose and ketone bodies in the metabolic control of experimental brain cancer. *British Journal of Cancer* 89, 1375-1382, doi:10.1038/sj.bjc.6601269 (2003).

19 Freedland, S. J. et al. Carbohydrate restriction, prostate cancer growth, and the insulin-like growth factor axis. *The Prostate* 68, 11-19, doi:10.1002/pros.20683 (2008).

20 Zuccoli, G. et al. Metabolic management of glioblastoma multiforme using standard therapy together with a restricted ketogenic diet: Case Report. *Nutrition & metabolism* 7, 7, doi:10.1186/1743-7075-7-33 (2010).

21 Schmidt, M., Pfetzer, N., Schwab, M., Strauss, I. & Kammerer, U. Effects of a ketogenic diet on the quality of life in 16 patients with advanced cancer: A pilot trial. *Nutrition & metabolism* 8, 54, doi:10.1186/1743-7075-8-54 (2011).

22 Raffaghello, L. et al. Starvation-dependent differential stress resistance protects normal but not cancer cells against high-dose chemotherapy. *Proc Natl Acad Sci USA*, doi:10.1073/pnas.0708100105 (2008).

23 Raffaghello, L. et al. Fasting and differential chemotherapy protection in patients. *Cell cycle* (Georgetown, Tex.) 9, 4474-4476 (2010).

24 Lee, C. & Longo, V. D. Fasting vs dietary restriction in cellular protection and cancer treatment: from model organisms to patients. *Oncogene* 30, 3305-3316, doi: 10.1038/onc.2011.91 (2011).

25 Lee, C. et al. Reduced levels of IGF-I mediate differential protection of normal and cancer cells in response to fasting and improve chemotherapeutic index. *Cancer Research* 70, 1564-1572, doi:10.1158/0008-5472.CAN-09-3228 (2010).

26 Safdie, F. M. et al. Fasting and cancer treatment in humans: A case series report. *Aging* 1, 988-1007 (2009).

27 Anson, R. M. et al. Intermittent fasting dissociates beneficial effects of dietary restriction on glucose metabolism and neuronal resistance to injury from calorie intake. *Proceedings of the National Academy of Sciences of the United States of America* 100, 6216-6220, doi:10.1073/pnas.1035720100 (2003).

28 Hashim, S. A. & Vanitallie, T. B. Ketone body therapy: from the ketogenic diet to the oral administration of ketone ester. *J Lipid Res* 55, 1818-1826, doi: 10.1194/jlr.R046599 (2014).

29 D'Agostino, D. P. et al. Therapeutic ketosis with ketone ester delays central nervous system oxygen toxicity seizures in rats. *American journal of physiology. Regulatory, integrative and comparative physiology* 304, R829-836, doi:10.1152/ajpregu.00506.2012 (2013).

30 Tipoe, G. L., Leung, T. M., Hung, M. W. & Fung, M. L. Green tea polyphenols as an anti-oxidant and anti-inflammatory agent for cardiovascular protection. *Cardiovascular & hematological disorders drug targets* 7, 135-144 (2007).

31 Aggarwal, B. B. & Harikumar, K. B. Potential therapeutic effects of curcumin, the anti-inflammatory agent, against neurodegenerative, cardiovascular, pulmonary, metabolic, autoimmune and neoplastic diseases. *The international journal of biochemistry & . . .* (2009).

32 Nallasamy, P. et al. Sulforaphane reduces vascular inflammation in mice and prevents TNF-α-induced monocyte adhesion to primary endothelial cells through interfering with the NF-κB pathway. *The Journal of nutritional biochemistry* 25, 824-833, doi: 10.1016/j.jnutbio.2014.03.011 (2014).

33 Yang, C., Wang, X., Lu, G. & Picinich, S. Cancer prevention by tea: animal studies, molecular mechanisms and human relevance. *Nat Rev Cancer*, doi:10.1038/nrc2641 (2009).

34 Fu, Y. & Koo, M. W. EGCG protects HT-22 cells against glutamate-induced oxidative stress. *Neurotoxicity research* 10, 23-30 (2006).

35 Schroeder, E. K. et al. Green tea epigallocatechin 3-gallate accumulates in mitochondria and displays a selective antiapoptotic effect against inducers of mitochondrial oxidative stress in neurons. *Antioxid Redox Signal* 11, 469-480, doi:10.1089/ARS.2008.2215 (2009).

36 Lee, S. J. & Lee, K. W. Protective effect of (−)-epigallocatechin gallate against advanced glycation end-products-induced injury in neuronal cells. *Biological & pharmaceutical bulletin* 30, 1369-1373 (2007).

37 Mandel, S., Weinreb, O., Amit, T. & Youdim, M. B. H. Cell signaling pathways in the neuroprotective actions of the green tea polyphenol (−)-epigallocatechin-3-gallate: implications for neurodegenerative diseases. *Signaling pathways in EGCG neuroprotection* 88, 1555-1569, doi:10.1046/j.1471-4159.2003.02291.x (2004).

38 Mandel, S. A. et al. Multifunctional activities of green tea catechins in neuroprotection. Modulation of cell survival genes, iron-dependent oxidative stress and PKC signaling pathway. *Neuro-Signals* 14, 46-60, doi:10.1159/000085385 (2005).

39 Menard, C., Bastianetto, S. & Quirion, R. Neuroprotective effects of resveratrol and epigallocatechin gallate polyphenols are mediated by the activation of protein kinase C gamma. *Frontiers in cellular neuroscience* 7, 281, doi: 10.3389/fncel.2013.00281 (2013).

39 Reznichenko, L., Amit, T., Youdim, M. B. & Mandel, S. Green tea polyphenol (−)-epigallocatechin-3-gallate induces neurorescue of long-term serum-deprived PC12 cells and promotes neurite outgrowth. *J Neurochem* 93, 1157-1167, doi:10.1111/j.1471-4159.2005.03085.x (2005).

40 Isbrucker, R. A., Bausch, J., Edwards, J. A. & Wolz, E. Safety studies on epigallocatechin gallate (EGCG) preparations. Part 1: genotoxicity. *Food and chemical toxicology:an international journal published for the British Industrial Biological Research Association* 44, 626-635, doi:10.1016/j.fct.2005.07.005 (2006).

41 Isbrucker, R. A., Edwards, J. A., Wolz, E., Davidovich, A. & Bausch, J. Safety studies on epigallocatechin gallate (EGCG) preparations. Part 2: dermal, acute and short-term toxicity studies. *Food and chemical toxicology: an international journal published for the British Industrial Biological Research Association* 44, 636-650, doi: 10.1016/j.fct.2005.11.003 (2006).

42 Isbrucker, R. A., Edwards, J. A., Wolz, E., Davidovich, A. & Bausch, J. Safety studies on epigallocatechin gallate (EGCG) preparations. Part 3: teratogenicity and reproductive toxicity studies in rats. *Food and chemical toxicology: an international journal published for the British Industrial Biological Research Association* 44, 651-661, doi: 10.1016/j.fct.2005.11.002 (2006).

43 Imai, K. & Nakachi, K. Cross sectional study of effects of drinking green tea on cardiovascular and liver diseases. *BMJ* 310, 693-696 (1995).

44 Maheshwari, R. K., Singh, A. K., Gaddipati, J. & Srimal, R. C. Multiple biological activities of curcumin: a short review. *Life Sciences* 78, 2081-2087, doi:10.1016/j.lfs.2005.12.007 (2006).

45 Kunnumakkara, A. B., Anand, P. & Aggarwal, B. B. Curcumin inhibits proliferation, invasion, angiogenesis and metastasis of different cancers through interaction with multiple cell signaling proteins. *Cancer letters* 269, 199-225, doi:10.1016/j.canlet.2008.03.009 (2008).

46 Al Moundhri, M. S., Al-Salam, S., Al Mahrouqee, A., Beegam, S. & Ali, B. H. The effect of curcumin on oxaliplatin and cisplatin neurotoxicity in rats: some behavioral, biochemical, and histopathological studies. *Journal of medical toxicology: official journal of the American College of Medical Toxicology* 9, 25-33, doi: 10.1007/s13181-012-0239-x (2013).

47 Mendonça, L. M. et al. Curcumin reduces cisplatin-induced neurotoxicity in NGF-differentiated PC12 cells. *Neuro Toxicology* 34, 205-211, doi:10.1016/j.neuro.2012.09.011 (2013).

48 Di Pierro, F. & Settembre, R. Safety and efficacy of an add-on therapy with curcumin phytosome and piperine and/or lipoic acid in subjects with a diagnosis of peripheral neuropathy treated with dexibuprofen. *Journal of Pain Research,* 497, doi:10.2147/JPR.S48432 (2013).

49 Zhao, X. et al. Curcumin exerts antinociceptive effects in a mouse model of neuropathic pain: descending monoamine system and opioid receptors are differentially involved. *Neuropharmacology* 62, 843-854, doi:10.1016/j.neuropharm.2011.08.050 (2012).

50 Zhao, W. C. et al. Curcumin ameliorated diabetic neuropathy partially by inhibition of NADPH oxidase mediating oxidative stress in the spinal cord. *Neurosci Lett* 560, 81-85, doi:10.1016/j.neulet.2013.12.019 (2014).

51 Joshi, R. P. et al. SNEDDS curcumin formulation leads to enhanced protection from pain and functional deficits associated with diabetic neuropathy: an insight into its mechanism for neuroprotection. *Nanomedicine* 9, 776-785, doi:10.1016/j.nano.2013.01.001 (2013).

53 Tu, X. K. et al. Curcumin Inhibits TLR2/4-NF-kappaB Signaling Pathway and Attenuates Brain Damage in Permanent Focal Cerebral Ischemia in Rats. *Inflammation*, doi:10.1007/s10753-014-9881-6 (2014).

54 Shah, B. H. et al. Inhibitory effect of curcumin, a food spice from turmeric, on platelet-activating factor- and arachidonic acid-mediated platelet aggregation through inhibition of thromboxane formation and Ca2+ signaling. *Biochemical pharmacology* 58, 1167-1172, doi:10.1016/50006-2952(99)00206-3 (1999).

55 Shankar, T. N., Shantha, N. V., Ramesh, H. P., Murthy, I. A. & Murthy, V. S. Toxicity studies on turmeric (Curcuma longa): acute toxicity studies in rats, guineapigs & monkeys. *Indian journal of experimental biology* 18, 73-75 (1980).

56 Deshpande, S. S., Ingle, A. D. & Maru, G. B. Chemopreventive efficacy of curcumin-free aqueous turmeric extract in 7,12-dimethylbenz[a]anthracene-induced rat mammary tumorigenesis. *Cancer letters* 123, 35-40, doi: 10.1016/50304-3835(97)00400-X (1998).

57 Cheng, A. L. et al. Phase I clinical trial of curcumin, a chemopreventive agent, in patients with high-risk or pre-malignant lesions. *Anticancer research* 21, 2895-2900 (2001).

58 Lao, C. D. et al. Dose escalation of a curcuminoid formulation. *BMC Complementary and Alternative Medicine* 6, 10-10, doi:10.1186/1472-6882-6-10 (2006).

59 Deodhar, S. D., Sethi, R. & Srimal, R. C. Preliminary study on antirheumatic activity of curcumin (diferuloyl methane). *The Indian journal of medical research* 71, 632-634 (1980).

60 Lal, B. et al. Efficacy of curcumin in the management of chronic anterior uveitis. *Phytotherapy research: PTR* 13, 318-322, doi:10.1002/(SICI)1099-1573(199906)13:4<318::AID-PTR445>3.0.00;2-7 (1999).

61 Holt, P. R. P., Katz, S. S. & Kirshoff, R. R. Curcumin therapy in inflammatory bowel disease: a pilot study.

62 Durgaprasad, S. S., Pai, C. G. C., Vasanthkumar, Alvres, J. F. J. & Namitha, S. S. A pilot study of the antioxidant effect of curcumin in tropical pancreatitis. *The Indian journal of medical research* 122, 315-318 (2005).

63 Getahun, S. M. & Chung, F. L. Conversion of glucosinolates to isothiocyanates in humans after ingestion of cooked watercress. *Cancer epidemiology, biomarkers & prevention: a publication of the American Association for Cancer Research, cosponsored by the American Society of Preventive Oncology* 8, 447-451 (1999).

64 Hanlon, N. et al. Absolute bioavailability and dose-dependent pharmacokinetic behaviour of dietary doses of the chemopreventive isothiocyanate sulforaphane in rat. *British Journal of Nutrition* 99, 559-564, doi:10.1017/S0007114507824093 (2007).

65 Hanlon, N., Coldham, N., Gielbert, A. & Sauer, M. Repeated intake of broccoli does not lead to higher plasma levels of sulforaphane in human volunteers. *Cancer letters* (2009).

66 Ho, E., Clarke, J. D. & Dashwood, R. H. Dietary sulforaphane, a histone deacetylase inhibitor for cancer prevention. *The Journal of nutrition* 139, 2393-2396, doi:10.3945/jn.109.113332 (2009).

67 Conaway, C., Wang, C., Pittman, B. & Yang, Y. Phenethyl Isothiocyanate and Sulforaphane and their N-Acetylcysteine Conjugates Inhibit Malignant Progression of Lung Adenomas Induced by Tobacco Carcinogens in A/J Mice. *Cancer Research* (2005).

68 Clarke, J. D., Hsu, A., Yu, Z., Dashwood, R. H. & Ho, E. Differential effects of sulforaphane on histone deacetylases, cell cycle arrest and apoptosis in normal prostate cells versus hyperplastic and cancerous prostate cells. *Molecular nutrition & food research* 55, 999-1009, doi:10.1002/mnfr.201000547 (2011).

69 Fimognari, C. Sulforaphane as a promising molecule for fighting cancer. *Mutation Research/Reviews in Mutation Research* (2007).

70 Song, M.-Y. M. et al. Sulforaphane protects against cytokine- and streptozotocin-induced beta-cell damage by suppressing the NF-kappaB pathway. 235, 57-67, doi:10.1016/j.taap.2008.11.007 (2009).

71 Nair, S. et al. Synergistic Effects of a Combination of Dietary Factors Sulforaphane and (−) Epigallocatechin-3-gallate in HT-29 AP-1 Human Colon Carcinoma Cells. *Pharmaceutical research* 25, 387-399, doi:10.1007/s11095-007-9364-7 (2007).

72 Dashwood, R. H. & Ho, E. Dietary agents as histone deacetylase inhibitors: sulforaphane and structurally related isothiocyanates. *Nutrition reviews* 66 Suppl 1, S36-38, doi:10.1111/j.1753-4887.2008.00065.x (2008).

73 Myzak, M., Dashwood, W., Orner, G. & Ho, E. Sulforaphane inhibits histone deacetylase in vivo and suppresses tumorigenesis in Apcmin mice. *The FASEB Journal* (2006).

74 Mulcahy, R. T., Wartman, M. A., Bailey, H. H. & Gipp, J. J. Constitutive and beta-naphthoflavone-induced expression of the human gamma-glutamylcysteine synthetase heavy subunit gene is regulated by a distal antioxidant response element/TRE sequence. *J Biol Chem* 272, 7445-7454 (1997).

75 Thimmulappa, R. K. et al. Identification of Nrf2-regulated genes induced by the chemopreventive agent sulforaphane by oligonucleotide microarray. *Cancer Res* 62, 5196-5203 (2002).

76 Bahadoran, Z. et al. Broccoli sprouts reduce oxidative stress in type 2 diabetes: a randomized double-blind clinical trial. *European Journal of Clinical Nutrition* 65, 972-977, doi:10.1038/ejcn.2011.59 (2011).

77 Miller, D. M., Singh, I. N., Wang, J. A. & Hall, E. D. Administration of the Nrf2-ARE activators sulforaphane and carnosic acid attenuates 4-hydroxy-2-nonenal-induced mitochondrial dysfunction ex vivo. *Free Radic Biol Med* 57, 1-9, doi:10.1016/j.freeradbiomed.2012.12.011 (2013).

78 Negi, G., Kumar, A. & Sharma, S. S. Nrf2 and NF-κB modulation by sulforaphane counteracts multiple manifestations of diabetic neuropathy in rats and high glucose-induced changes. *Current neurovascular research* 8, 294-304 (2011).

79 Ping, Z. et al. Sulforaphane protects brains against hypoxic-ischemic injury through induction of Nrf2-dependent phase 2 enzyme. *Brain Res* 1343, 178-185, doi:10.1016/j.brainres.2010.04.036 (2010).

80 Myzak, M. C., Tong, P., Dashwood, W.-M., Dashwood, R. H. & Ho, E. Sulforaphane retards the growth of human PC-3 xenografts and inhibits HDAC activity in human subjects. *Experimental biology and medicine* (Maywood, N.J.) 232, 227-234 (2007).

81 Puchowicz, M. A. et al. Dog model of therapeutic ketosis induced by oral administration of R,S-1,3-butanediol diacetoacetate. *J Nutr Biochem* 11, 281-287 (2000).

What is claimed:

1. A method for managing negative side effects of chemotherapy, radiation therapy, or both, in a subject having cancer, wherein said method comprises administering an effective amount of: (a) epigallocatechin-3-gallate (EGCG), (b) curcumin, and (c) sulforaphane (SFN) to a subject having cancer and undergoing chemotherapy, radiation therapy, or both, for treatment of the cancer, wherein said administering delays, inhibits, or reverses a negative side effect of the chemotherapy, radiation therapy, or both.

2. The method of claim 1, wherein the EGCG, curcumin and SFN are provided as powder, capsules, tablets, caplets, gel, oil, liquid, emulsion, drink, liquid food product or solid food product.

3. The method of claim 2, wherein the EGCG, curcumin, and SFN are administered in the form of a unit dosage or separate formulations administered to the subject simultaneously or sequentially.

4. The method of claim 1, wherein the SFN is administered to the subject in the form of broccoli sprouts or broccoli sprout powder.

5. The method of claim 1, further comprising administering (d) a medium chain triglyceride (MCT) to the subject.

6. The method of claim 5, wherein the subject is on a ketogenic diet or modified ketogenic diet.

7. The method of claim 1, wherein the subject is on a ketogenic diet or modified ketogenic diet.

8. The method of claim 1, wherein the EGCG, curcumin, and SFN are administered together in a composition that is orally administered to the subject.

9. The method of claim 1, wherein the treatment comprises chemotherapy.

10. The method of claim 1, wherein the treatment comprises radiation therapy.

11. The method of claim 1, wherein the negative side effect is one or more negative side effects selected from among: anemia, leukopenia, thrombocytopenia, nephrotoxicity, hepatotoxicity, neurotoxicity, peripheral neuropathy, and chemotoxicity to endogenous stem cells.

12. The method of claim 1, wherein the subject is human.

13. The method of claim 1, wherein the subject is a non-human animal.

14. The method of claim 1, wherein the negative side effect is one or more negative side effects selected from among: anemia, leukopenia, and peripheral neuropathy.

15. The method of claim 14, wherein said administering comprises orally administering a composition to the subject, wherein the composition comprises each of the EGCG, curcumin, and SFN.

16. The method of claim 9, wherein the chemotherapy comprises oxaliplatin or paclitaxel.

17. The method of claim 9, wherein the chemotherapy comprises temozolomide.

18. The method of claim 9, wherein the chemotherapy comprises fluorouracil.

19. The method of claim 1, wherein the method further comprises orally administering a ketone body or ketone ester to the subject.

20. The method of claim 4, wherein the method further comprises orally administering a ketone body or ketone ester to the subject.

* * * * *

UNITED STATES PATENT AND TRADEMARK OFFICE
CERTIFICATE OF CORRECTION

PATENT NO. : 11,020,372 B2  
APPLICATION NO. : 15/078590  
DATED : June 1, 2021  
INVENTOR(S) : Loic Pierre Deleyrolle and Brent Allan Reynolds Page 1 of 1

It is certified that error appears in the above-identified patent and that said Letters Patent is hereby corrected as shown below:

In the Specification

Column 2,
Line 58, "half corning" should read --half coming--.

Column 3,
Line 23, "##, p<0.01," should read --$^{\#\#}$, $^{\#}$, p<0.01,--.

Column 12,
Line 27, "Paliferm in," should read --Palifermin,--.
Line 40, "Rom iplostim" should read --Romiplostim--.

Signed and Sealed this  
Fifth Day of October, 2021

Drew Hirshfeld  
*Performing the Functions and Duties of the*  
*Under Secretary of Commerce for Intellectual Property and*  
*Director of the United States Patent and Trademark Office*